United States Patent [19]

Baker et al.

[11] Patent Number: 5,324,723

[45] Date of Patent: Jun. 28, 1994

[54] OXAZOLES AND THIAZOLES FOR THE TREATMENT OF SENILE DEMENTIA

[75] Inventors: Raymond Baker, Much Hadham; John Saunders, Bishop's Stortford, both of England; Roger J. Snow, Danbury, Conn.; Graham A. Showell, Welwyn Garden City, England

[73] Assignee: Merck Sharpe & Dohme Ltd., Hoddesdon

[21] Appl. No.: 86,389

[22] Filed: Jul. 1, 1993

Related U.S. Application Data

[63] Continuation of Ser. No. 912,469, Jul. 13, 1992, abandoned, which is a continuation of Ser. No. 454,492, Feb. 5, 1990, abandoned, which is a continuation of Ser. No. 239,892, Sep. 2, 1988, abandoned, which is a continuation of Ser. No. 454,492, Feb. 5, 1990, abandoned, which is a continuation of Ser. No. 239,892, Sep. 2, 1988, abandoned.

[30] Foreign Application Priority Data

Sep. 10, 1987 [GB] United Kingdom ............ 8721343
Jan. 27, 1988 [GB] United Kingdom ............ 8801759

[51] Int. Cl.$^5$ .............. C07D 453/02; C07D 487/08; A61K 31/435; A61K 31/41

[52] U.S. Cl. .................. 514/212; 514/214; 514/299; 514/304; 514/305; 514/326; 514/340; 514/342; 514/365; 514/369; 514/370; 514/374; 514/376; 514/377; 546/125; 546/133; 546/137; 546/112; 546/209; 546/215; 546/280; 548/181; 548/182; 548/186; 548/187; 548/194; 548/200; 548/201; 548/202; 548/203; 548/204; 548/205; 548/228; 548/229; 548/232; 548/233; 548/225; 548/236; 540/556; 540/603

[58] Field of Search ............ 546/112, 125, 133, 137, 546/209, 215, 280; 548/181, 182, 186, 187, 194, 200, 201, 202, 203, 204, 205, 225, 228, 229, 232, 233, 236; 540/556, 603; 514/212, 214, 299, 304, 305, 326, 340, 342, 365, 369, 370, 374, 376, 377

[56] References Cited

U.S. PATENT DOCUMENTS

4,650,805 3/1987 Jaen et al. .................. 514/326
4,968,691 11/1990 Orlek et al. ................. 514/305

FOREIGN PATENT DOCUMENTS

244018 11/1987 European Pat. Off.
261763 3/1988 European Pat. Off.

*Primary Examiner*—Marianne M. Cintins
*Assistant Examiner*—Catherine S. Kilby Scalzo
*Attorney, Agent, or Firm*—Robert J. North; Melvin Winokur

[57] ABSTRACT

1,3-Oxazole and 1,3-thiazole compounds of formula I, and their pharmaceutically acceptable salts and prodrugs:

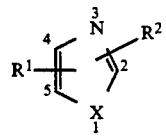

wherein
X represents oxygen or sulphur;
$R^1$ represents a non-aromatic azacyclic or azabicyclic ring system.

10 Claims, No Drawings

OXAZOLES AND THIAZOLES FOR THE TREATMENT OF SENILE DEMENTIA

CROSS REFERENCE TO RELATED APPLICATIONS

This is a continuation of U.S. Ser. No. 07/912,469, filed on Jul. 13, 1992, now abandoned, which is a continuation of U.S. Ser. No. 07/454,492 filed Feb. 5, 1990, now abandoned, which is a continuation of U.S. Ser. No. 07/239,892, filed on Sep. 2, 1988, now abandoned.

The present invention relates to a class of substituted oxazole and thiazole compounds which stimulate central muscarinic acetylcholine receptors and therefore are useful in the treatment of neurological and mental illnesses whose clinical manifestations are due to cholinergic deficiency. Such diseases include presenile and senile dementia (also known as Alzheimer's disease and senile dementia of the Alzheimer type respectively), Huntington's chorea, tardive dyskinesia, hyperkinesia, mania and Tourette Syndrome. Alzheimer's disease, the most common dementing illness, is a slowly progressive neurological disorder characterised by marked deficits in cognitive functions including memory, attention, language and visual perception capabilities. The compounds of this invention are also useful analgesic agents and therefore useful in the treatment of severe painful conditions such as rheumatism, arthritis and terminal illness.

Compounds capable of enhancing muscarinic cholinergic transmission in the cortex should be beneficial in reversing the cholinergic deficiency in Alzheimer's disease and other diseases related to cholinergic dysfunction. However, most muscarinic ligands, including acetylcholine itself, are quaternary ammonium compounds incapable of penetrating the blood-brain barrier to any clinically significant extent following peripheral (e.g. oral) administration. Such agents fail to stimulate the desired central sites but instead induce undesired side-effects mediated exclusively by peripherally-located muscarinic acetylcholine receptors.

The oxazole and thiazole compounds of the present invention stimulate cholinergic transmission but, being either secondary or tertiary amines with physiochemical properties (lipophilicity and pKa) consistent with CNS penetrability, can stimulate those central sates implicated in neurodegenerative disorders. It is believed that the enhancement of cholinergic transmission demonstrated by the compounds of this invention is achieved either directly by stimulating postsynaptic receptors, or indirectly by potentiating acetylcholine release.

Most of the oxazoles and thiazoles which possess this activity are novel compounds, although certain piperidinyl- and tetrahydropyridinyl-substituted oxazoles and thiazoles are known from U.S. Pat. No. 4,650,805 and from EP-A-0244018. These published on 30 Mar. 1988, describes a class of compounds which are stated to be of use in the treatment of psychosis and disorders of the central nervous system, such as schizophrenia, Parkinson's disease and depression. That activity does not, however, suggest that any of these compounds could be muscarinic agonists.

In addition, EP-A-0261763, which was published on 30 March 1988, describes a class of compounds which include oxazoles and thiazoles having particular exo-azabicyclic substituents. These compounds are stated to be of potential use in the treatment and/or prophylaxis of dementia in mammals.

The present invention provides the use of a 1,3-oxazole or 1,3-thiazole of structural formula I, or a pharmaceutically acceptable salt or prodrug thereof:

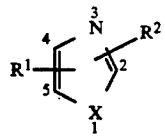

(I)

wherein
X represents oxygen or sulphur;
$R^1$ represents a non-aromatic azacyclic or azabicyclic ring system; and
$R^2$ represents hydrogen, halogen, $-CF_3$, $-OR^7$, $-NR^7R^8$, $-NHOR^7$, $-NHNH_2$, $-CN$, $-CO_2R^7$ or $-CONR^7R^8$, or a substituted or unsubstituted, saturated or unsaturated hydrocarbon group; wherein $R^7$ and $R^8$ independently represent hydrogen or $C_{1-2}$ alkyl;
provided that:
(a) when $R^2$ is hydrogen and $R^1$ is in the 2-position, then $R^1$ is in the endo configuration; and
(b) when $R^2$ is methyl and $R^1$ is in the 2-position, then $R^1$ does not represent an unsubstituted exo-1-azabicyclo[2.2.1]hept-3-yl, exo-1-azabicyclo[3.2.1]oct-3-yl or exo-1-azabicyclo[3.2.1]oct-6-yl group;
for the preparation of a medicament useful for the treatment of neurological and mental illnesses whose clinical manifestations are due to involvement of cholinergic neurones.

The present invention also provides a novel 1,3-oxazole or 1,3-thiazole represented by the structural formula II, or a salt or prodrug thereof:

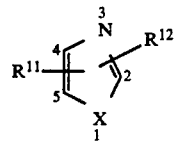

(II)

wherein
X is oxygen or sulphur;
$R^{11}$ represents a non-aromatic azacyclic or azabicyclic ring system; and
$R^{12}$ represents hydrogen, halogen, $-CF_3$, $-OR^7$, $-NR^7R^8$, $-NHOR^7$, $-NHNH_2$, $-CN$, $-CO_2R^7$ or $-CONR^7R^8$ or an optionally substituted, saturated or unsaturated hydrocarbon group; wherein $R^7$ and $R^8$ are as defined above;
provided that when $R^{12}$ is present in the 2-position and represents amino, alkylamino, dialkylamino or alkylcarbonylamino, then $R^{11}$, when present in the 4-position, does not represent optionally N-substituted piperidin-3-yl or 1,2,5,6-tetrahydropyridin-3-yl;
provided also that:
(a) when $R^{12}$ is hydrogen and $R^{11}$ is in the 2-position, then $R^{11}$ is in the endo configuration; and
(b) when $R^{12}$ is methyl and $R^{11}$ is in the 2-position, then $R^{11}$ does not represent an unsubstituted exo-1-azabicyclo[2.2.1]hept-3-yl, exo-1-azabicyclo[3.2.1]oct-3-yl or exo-1-azabicyclo[3.2.1]oct-6-yl group.

The azacyclic or azabicyclic ring system for the groups $R^1/R^{11}$ is a non-aromatic ring system containing one nitrogen atom as the sole heteroatom. Suitably the ring system contains from 4 to 10 ring atoms, preferably from 5 to 8 ring atoms. Preferably, the ring system contains a tertiary amino nitrogen atom in a caged structure. The bicyclic systems may be fused, spiro or bridged. Preferably, the nitrogen atom is at a bridgehead in a bicyclic system. Examples of suitable azacyclic or azabicyclic ring systems include the following:

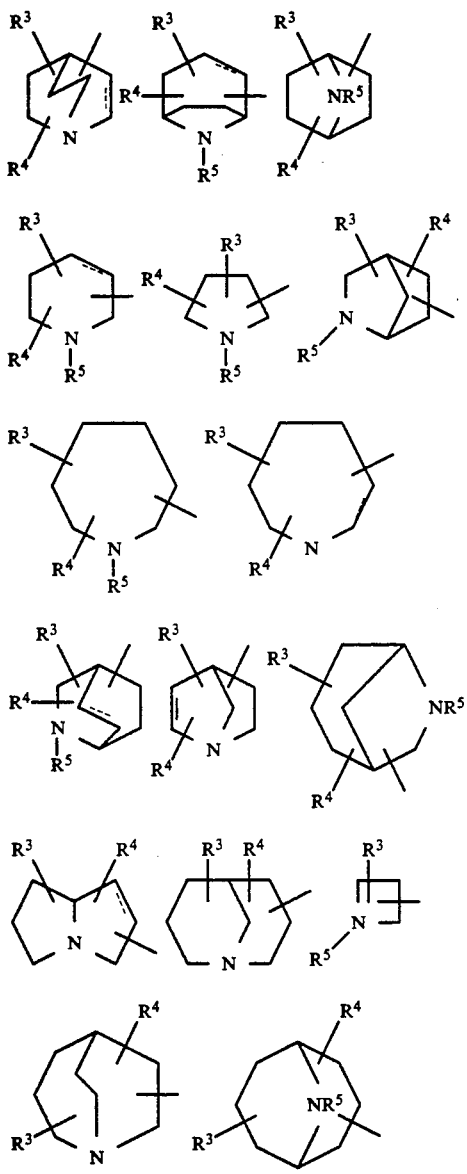

wherein the broken line represents an optional chemical bond;
the substituents $R^3$ and $R^4$ may be present at any position, including the point of attachment to the oxazole or thiazole ring, and independently represent hydrogen, $C_{1-4}$ alkyl, halo, $C_{1-4}$ alkoxy, hydroxy or carboxy; or $R^3$ and $R^4$ together represent carbonyl; and
the group $R^5$ represents hydrogen or $C_{1-4}$ alkyl.

It will be appreciated that the nitrogen atom in the azacyclic or azabicyclic ring system will carry a lone pair of electrons.

Suitably the group $R^3$ is hydrogen or methyl; and $R^4$ is hydrogen, methyl or hydroxy. Preferably one or both of $R^3$ and $R^4$ is hydrogen.

Preferably the group $R^5$ represents hydrogen or methyl.

Suitably the azacyclic or azabicyclic ring system is a pyrrolidine, piperidine, tetrahydropyridine, azanorbornane, quinuclidine or 1-azabicyclo[3.2.1]octane ring system. Preferred values for the azacyclic or azabicyclic ring system are tetrahydropyridine, 1-azanorbornane and quinuclidine, in particular either unsubstituted or substituted with methyl or hydroxy.

The substituent $R^2$ or $R^{12}$ on the oxazole or thiazole ring may be a substituent of low lipophilicity. The term "low lipophilicity" is intended to indicate that the group has a Rekker f value (hydrophobic fragment constant; see R. F. Rekker, "The Hydrophobic Fragmental Constant", Elsevier, 1977) of not greater than 1.5. For example, the methyl group has a value of 0.7 and the ethyl group a value of 1.26.

Thus the substituent of low lipophilicity may be, for example, hydrogen, halogen, —$CF_3$, —$OR^7$, —$NR^7R^8$, —$NHOR^7$, —$NHNH_2$, —CN, —$CO_2R^7$, —$CONR^7R^8$, $C_{2-5}$ alkenyl, $C_{2-5}$ alkynyl, $C_{1-2}$ alkyl, or $C_{1-2}$ alkyl substituted with —$OR^7$, —$NR^7R^8$, —$SR^7$, —$CO_2R^7$, —$CONR^7R^8$ or halogen; wherein $R^7$ and $R^8$ are as defined above with respect to formula I.

Alternatively the group $R^2$ or $R^{12}$ may represent an optionally substituted saturated hydrocarbon group having at least three carbon atoms, or unsaturated hydrocarbon group having at least 6 carbon atoms.

Thus when the group $R^2$ or $R^{12}$ is a hydrocarbon substituent, it may be $C_{1-15}$ alkyl, $C_{2-15}$ alkenyl, $C_{2-15}$ alkynyl, aryl or aralkyl. The alkyl alkenyl or alkynyl groups may be straight, branched or cyclic groups. Suitably the alkyl group comprises from 1 to 6 carbon atoms. The hydrocarbon group may carry one or more substituents. Suitable substituent groups for the hydrocarbon group include halogen, —$OR^6$, —$CF_3$, —$NR^6R^9$, —$NO_2$, optionally substituted aryl, keto, —$SR^6$, —$SOR^6$, —$SO_2R^6$, —$CO_2R^6$ and —$CONR^6R^9$; wherein $R^6$ is hydrogen or $C_{1-6}$ alkyl and $R^9$ is hydrogen, $C_{1-6}$ alkyl or —$COCH_3$.

Substituents most suitable for the aryl group include chloro, bromo, methoxy $C_{1-6}$ alkyl methoxycarbonyl, trifluoromethyl, nitro and -$NR^6R^7$.

Preferably the group $R^2$ or $R^{12}$ is hydrogen, halogen, —$CF_3$, —$OR^7$, —$NR^7R^8$, —$NHNH_2$, —CN, —$CO_2R^7$, —$CONR^7R^8$, phenyl ($C_{1-3}$) alkyl, $C_{3-6}$ cycloalkyl, adamantyl, $C_{2-6}$ alkenyl, $C_{2-6}$ alkynyl, $C_{1-6}$ alkyl, or $C_{1-6}$ alkyl substituted with —$OR^6$, —$NHR^6$, —$SR^6$, —$CO_2R^6$, —$CON(R^6)_2$ or halogen. Particular values of this group are hydrogen, methyl, ethyl, isopropyl, cyclopropyl, benzyl, 1-phenylethyl, adamantyl, amino, methoxycarbonyl and ethoxycarbonyl. Preferred values are hydrogen, methyl, ethyl and amino.

One group of prodrugs of compounds of this invention have a substituent on the oxazole or thiazole ring which is hydrolysable in vivo to an amino group.

Groups which are hydrolysable in vivo to an amino group on the compounds of this invention may be readily ascertained by administering the compound to a human or animal and detecting, by conventional analytical techniques, the presence of the corresponding compound having an amino substituent in the urine of a human or animal. Examples of such groups include, for example, amido and urethane substituents, in particular a group of formula —NH.Q, wherein Q represents CHO, COR or CO$_2$R, and R represents an optionally substituted hydrocarbon group.

In this context, the hydrocarbon group R includes groups having up to 20 carbon atoms, suitably up to 10 carbon atoms, conveniently up to 6 carbon atoms. Suitable groups R include C$_{1-9}$ alkyl, C$_{2-6}$ alkenyl, C$_{2-6}$ alkynyl, C$_{3-7}$ cycloalkyl, C$_{3-7}$ cycloalkyl (C$_{1-6}$) alkyl, aryl, and aryl (C$_{1-6}$) alkyl. The alkyl group R may be straight or branched chain and may contain, for example, up to 12 carbon atoms, suitably from 1 to 6 carbon atoms. In particular the group may be substituted methyl, ethyl, n- or iso-propyl, n-, sec-, iso- or tert-butyl, n- or iso-heptyl, or n- or iso-octyl. Suitable cycloalkyl groups include cyclopentyl and cyclohexyl. The aryl group R includes phenyl and naphthyl optionally substituted with up to five, preferably up to three, substituent groups.

One sub-class of novel compounds within the scope of the present invention is represented by formula (III):

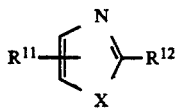

(III)

wherein X, R$^{11}$ and R$^{12}$ are as defined above; in particular wherein R$^{11}$ represents tetrahydropyridine, 1-azanorbornane, quinuclidine or 1-azabicyclo[3.2.1]octane, any of which groups R$^{11}$ may be optionally substituted with C$_{1-3}$ alkyl, or hydroxy; and R$^{12}$ represents hydrogen, C$_{1-6}$ alkyl (preferably methyl), phenyl(C$_{1-3}$)alkyl, C$_{3-6}$ cycloalkyl, amino, hydroxy, or C$_{1-3}$ alkoxy. Preferably R$^{11}$ represents tetrahydropyridine, quinuclidine or 1-azanorbornane.

A further subclass of compounds of this invention is represented by the formula (IV):

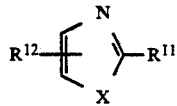

(IV)

wherein X, R$^{11}$ and R$^{12}$ are as defined above.

Within formula IV preferably R$^{11}$ represents tetrahydropyridine, quinuclidine, 1-azanorbornane or 1-azabicyclo[3.2.1]octane, any of which groups R$^{11}$ may be optionally substituted with C$_{1-3}$ alkyl or hydroxy. Preferably R$^{12}$ is hydrogen, amino, hydroxy, methyl or ethyl.

Specific compounds within the scope of the present invention include:
3-[4-(2-amino-1,3-thiazol)-yl]quinuclidine;
3-[4-(1,3-thiazol)-yl]quinuclidine;
3-[4-(2-amino-1,3-thiazol)-yl]pyrrolidine;
3-[4-(2-amino-1,3-thiazol)-yl]-1-methylpyrrolidine;
3-[4-(2-methyl-1,3-thiazol)-yl]quinuclidine;
3-[4-(2-hydroxy-1,3-thiazol)-yl]quinuclidine;
3-[5-(2-methyl-1,3-thiazol)-yl]quinuclidine;
3-[4-(2-amino-1,3-thiazol)-yl]-1-azabicyclo[2.2.1]heptane;
3-[5-(2-methyl-1,3-oxazol)-yl]quinuclidine;
3-[5-(2-methyl-1,3-oxazol)-yl]-1-azabicyclo[2.2.1]heptane;
3-[4-(2-methyl-1,3-oxazol)-yl]quinuclidine;
3-[4-(2-amino-1,3-oxazol)-yl]quinuclidine;
3-[2-(4-methyl-1,3-thiazol)-yl]quinuclidine;
3-[2-(4-methyl-1,3-oxazol)-yl]quinuclidine;
3-[2-(5-methyl-1,3-oxazol)-yl]quinuclidine;
3-[2-(4-methyl-1,3-thiazol)-yl]-1-azabicyclo[2.2.2]oct-2ene;
3-hydroxy-3-[2-(4-methyl-1,3-oxazol)-yl]quinuclidine;
(+)-3-[2-(4-methyl-1,3-oxazol)-yl]quinuclidine;
(−)-3-[2-(4-methyl-1,3-oxazol)-yl]quinuclidine;
3-hydroxy-3-[2-(1,3-oxazol)-yl]quinuclidine;
3-hydroxy-3-[2-(4-ethyl-1,3-oxazol)-yl]quinuclidine;
3-[2-(4-ethyl-1,3-oxazol)-yl]quinuclidine;
3-hydroxy-3-[2-(4-methyl-1,3-thiazol)-yl]quinuclidine;
1-methyl-3-[2-(5-methyl-1,3-oxazol)-yl]piperidine;
1-methyl-3-[2-(5-methyl-1,3-oxazol)-yl]-1,2,5,6-tetrahydropyridine;
3-[2-(5-methyl-1,3-oxazol)-yl]-1,2,5,6-tetrahydropyridine;
1-methyl-3-[4-(2-methyl-1,3-thiazol)-yl]-1,2,5,6-tetrahydropyridine;
3-[4-(2-methyl-1,3-thiazol)-yl]-1,2,5,6-tetrahydropyridine;
1-methyl-3-[4-(2-methyl-1,3-oxazol)-yl]-1,2,5,6-tetrahydropyridine;
3-[4-(2-methyl-1,3-oxazol)-yl]-1,2,5,6-tetrahydropyridine;
1-methyl-3-[2-(4-methyl-1,3-oxazol)-yl]-1,2,5,6-tetrahydropyridine;
1-methyl-3-[5-(2-methyl-1,3-oxazol)-yl]-1,2,5,6-tetrahydropyridine;
3-[2-(4-methyl-1,3-oxazol)-yl]-1,2,5,6-tetrahydropyridine;
3-[5-(2-methyl-1,3-oxazol)-yl]-1,2,5,6-tetrahydropyridine;
and salts and prodrugs thereof.

Most of the compounds of this invention have at least one asymmetric centre and often more than one; and can therefore exist as both enantiomers and diastereoisomers. In particular, those compounds possessing an unsymmetrical azabicyclic ring system may exist as exo and endo diastereoisomers. The oxazoles and thiazoles having a hydroxy substituent are likely to exist in a tautomeric form having a keto group, for example:

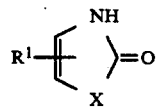

It is to be understood that the invention covers all such isomers, mixtures thereof, and tautomeric forms.

Also included within the scope of the present invention are salts of the novel compounds. It will be appreciated that salts of the compounds for use in medicine will be non-toxic pharmaceutically acceptable salts. Other salts may, however, be useful in the preparation of the compounds of the invention or their non-toxic pharmaceutically acceptable salts. Acid addition salts, for example,-may be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid or phosphoric acid. Where the novel compound carries a carboxylic acid group the invention also contemplates salts thereof, preferably non-toxic pharmaceutically acceptable salts thereof, such as the sodium, potassium and calcium salts thereof.

Salts of amine groups may also comprise the quaternary ammonium salts in which the amino nitrogen atom carries an alkyl, alkenyl, alkynyl or aralkyl group. Such quaternary ammonium derivatives penetrate poorly into the central nervous system and are therefore useful as peripherally selective muscarinic agents, useful for example as antispasmodic agents, agents to reduce gastric acid secretion, agents to block the muscarinic actions of acetylcholinesterase inhibitors in the treatment of myasthenia gravis and as agents to co-administer with muscarinic agonists in Alzheimer's disease.

It is believed that those compounds of formula I above which directly stimulate post-synaptic receptors are particularly useful as analgesic agents.

The method of treatment of this invention comprises the treatment of neurological disorders associated with a deficiency of acetylcholine, and includes a method of treating Alzheimer's disease, senile dementia of the Alzheimer type, Huntington's chorea, tardive dyskinesia, hyperkinesia, mania or Tourette syndrome by the administration to a patient in need of such treatment of an effective amount of one or more of the compounds of formula I above.

The invention further provides a method of treating severe painful conditions (e.g. rheumatism, arthritis and terminal illness) which comprises administering to a patient in need of analgesic treatment an effective amount of one or more of the compounds of formula I above.

This invention therefore also provides a pharmaceutical composition comprising a compound of formula II above and a pharmaceutically acceptable carrier.

It may, where appropriate, be advantageous, in order to reduce unwanted peripherally mediated side-effects, to incorporate into the composition a peripherally acting cholinergic antagonist (or anti-muscarinic agent). Thus the compounds of formula I may advantageously be administered together with a peripheral cholinergic antagonist such as N-methylscopolamine, N--methylatropine, propantheline, methantheline or glycopyrrolate.

The compounds of formula I can be administered orally, parenterally or rectally at a daily dose of about 0.01 to 10 mg/kg of body weight, preferably about 0.1 to 1 mg/kg, and may be administered on a regimen of 1–4 times a day. When a cholinergic antagonist is administered, it is incorporated at its conventional dose.

The pharmaceutical formulations of this invention preferably are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups and flavoured emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinyl-pyrrolidone and gelatin.

The novel compounds of this invention may be prepared by a process which comprises reacting a compound of formula $R^aCO.CH_2Y$, wherein Y represents bromo, chloro, or iodo; with a compound of formula $R^bCX.NH_2$, wherein X is as hereinbefore defined, and one of $R^a$ and $R^b$ represents a group $R^{11}$ and the other represents a group $R^{12}$. The reaction may be carried out in a suitable solvent, such as ethanol or acetic acid, or in a melt at a temperature of from 40° C. to 140° C. This process is better suited to the preparation of thiazoles but may also be employed for oxazoles (see Sharanin, Zh. Org. Chim., 1980, 16, 2185; and Kerr et al., J. Am. Chem. Soc., 1960, 82, 186). The α-halocarbonyl compounds of formula $R^aCO.CH_2Y$ may be prepared by halogenation of a methyl ketone $R^aCOCH_3$.

The novel compounds of the invention may also be prepared by cyclisation of an acylaminoketone of formula $R^aCOCH_2NHCOR^b$. If the cyclisation is carried out with the insertion of sulphur, in the presence of a dehydrating sulphide such as phosphorus pentasulphide, the product of the reaction is a thiazole. In this case the reaction is carried out either in a melt or in a suitable solvent, such as toluene, at a temperature of from 40° C. to 140° C. Alternatively if the compound $R^aCOCH_2NHCOR^b$ is cyclised in the presence of a dehydrating agent such as concentrated sulphuric acid, polyphosphoric acid, anhydrous hydrogen fluoride, phosphorus pentachloride, phosphorus oxychloride or thionyl chloride, the product of the reaction is an oxazole. In this case, the reaction may be carried out either in the absence of solvent or in a suitable solvent such as acetic anhydride. The acylaminoketone of formula $R^aCOCH_2NHCOR^b$ may be prepared by acylation of an aminoketone $R^aCOCH_2NH_2$ which in turn may be prepared from an α-halocarbonyl compound $R^aCOCH_2Y$ described above, by reaction with ammonia or sodium azide followed by reduction. The aminoketone $R^aCOCH_2NH_2$ may also be prepared by means of a Neber rearrangement reaction, which involves treatment of the corresponding oxime tosylate $R^aC(=N-OTS)CH_3$ with a strong base such as potassium ethoxide. Alternatively, the aminoketone $R^a\text{-}COCH_2NH_2$ may be prepared by reacting an acid chloride of formula $R^aCOCl$ with an anion of an alkyl isocyanate followed by acid hydrolysis.

A further method for the preparation of the novel oxazoles and thiazoles of this invention comprises the dehydroxylation of a compound of formula V:

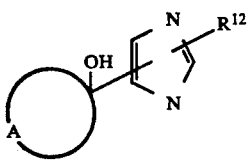

(V)

wherein $R^{12}$ and X are as defined above, and A represents the residue of an azacyclic or azabicyclic ring. The hydroxy group in compound V may be removed by chlorination and elimination, followed by hydrogenation. For example, chlorination and elimination may be effected by treatment with phosphorus oxychloride in the presence of triethylamine, or with thionyl chloride followed by DBN. The unsaturated product may then be hydrogenated under conventional conditions, such as over 10% palladium/carbon in methanol. Alternatively, the compound V may be dehydroxylated by the use of thionyl chloride followed by treatment with tributyltin hydride in a solvent such as tetrahydrofuran in the presence of a radical initiator such as azabisisobutyronitrile.

The compound of formula V may be prepared by reaction of a ketone compound of formula VI with a metal derivative of an oxazole or thiazole of formula VII:

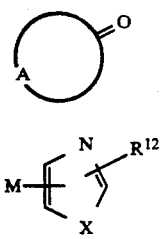

(VI)

(VII)

wherein A, $R^{12}$ and X are as defined above, and M represents a metal atom, for example lithium. The lithium derivative for instance may be prepared by reacting the corresponding chloro-substituted oxazole or thiazole with n-butyl lithium.

For the preparation of a compound of formula VII wherein the lithium atom represented by the group M is present in the 2-position of the oxazole or thiazole nucleus, it may be appropriate to react the corresponding oxazole or thiazole unsubstituted in the 2-position directly with n-butyl lithium. The preparation of the required 2-unsubstituted oxazole or thiazole starting material is illustrated in general terms by a method for preparing 2-unsubstituted oxazoles VIII described by J. W. Cornforth and R. H. Cornforth in J. Chem. Soc., 1953, 93. This method essentially involves reacting the α-chloro-β-ketoester IX with ammonium formate in the presence of formic acid, followed by decarboxylation of the resulting ester X under basic conditions with subsequent heating to reflux temperature in quinoline in the presence of a copper catalyst:

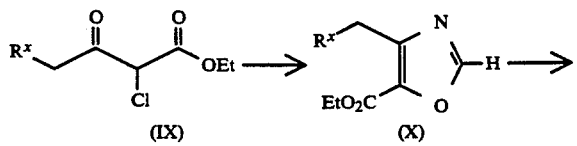

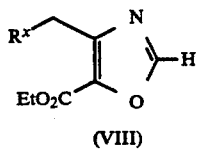

(VIII)

wherein $R^x$ is a group such that $-CH_2R^x$ represents the group $R^{12}$ as defined above.

The novel oxazoles of this invention may be prepared by cyclisation of a ketal of formula $R^a\text{-}COCH_2NHCR^bR^fR^g$ in which $R^f$ and $R^g$ independently represent $C_{1-4}$ alkoxy. The reaction is conveniently carried out by heating the ketal in the presence of a suitable mineral acid catalyst at a temperature in the region of 140° C. The ketal may in turn be prepared by reacting the aminoketone of formula $R^aCOCH_2NH_2$ with an orthoester of formula $R^bCR^fR^gR^h$ in which $R^f$, $R^g$ and $R^h$ independently represent $C_{1-4}$alkoxy. Under appropriate reaction conditions, the cyclisation will take place spontaneously in situ, without the necessity for isolation of the intermediate ketal of formula $R^a\text{-}COCH_2NHCR^bR^fR^g$.

The novel oxazoles of the present invention may also be prepared by reacting an aldehyde of formula $R^aCHO$ with the anion of an isonitrile of formula $L-CH_2N=C(Z)R^b$, where L is a leaving group such as toluenesulphonyl, and Z is methoxy or methylthio. Suitable solvents include tetrahydrofuran, dimethylsulphoxide and dimethoxyethane.

The novel oxazoles of this invention in which the group $R^{12}$ represents an optionally monosubstituted methyl group in the 5-position may be prepared by the cyclisation of a propargyl amide of formula XI:

$$R^{11}CONHCH_2C\equiv CR^x \qquad (XI)$$

wherein $R^{11}$ and $R^x$ are as defined above. The cyclisation may be carried out for example by treatment of the compound XI with a catalyst such as mercuric acetate in acetic acid.

The novel oxazoles of this invention in which the group $R^{12}$ represents an optionally monosubstituted methyl group in the 4-position may be prepared by a process which comprises reacting a cyano compound of formula $R^{11}CN$ with a propargyl alcohol of formula $HOCH_2C\equiv CR^x$, wherein $R^{11}$ and $R^x$ are as defined above. The reaction is conveniently carried out in the presence of an acidic catalyst such as, for example, sulphuric acid.

After any of the above described processes is complete, one substituent of low lipophilicity can be converted to another. For example an amino group may be converted to chloro, or hydrazo, $-NHNH_2$, via the intermediacy of diazonium, $-N_2$. Similarly, a chloro substituent may be converted, by reaction with a nucleophile such as methoxide, to methoxy, which can be converted to hydroxy under acidic conditions; and alkoxycarbonyl groups may be converted, via carboxy, to an amino substituent, —NH₂.

In any of the above reactions it may be necessary and/or desirable to protect any sensitive groups in the compounds. For example, if $R^a$ and/or $R^b$ include amino, carboxy, hydroxy or thiol groups, these may be protected in conventional manner. Thus, suitable protecting groups for hydroxy groups include silyl groups such as trimethylsilyl or tert-butyldimethylsilyl, and etherifying groups such as tetrahydropyranyl; and for amino groups include benzyloxycarbonyl and tert-butyloxycarbonyl. Carboxy groups are preferably protected in a reduced form such as in the form of their corresponding protected alcohols, which may be subsequently oxidised to give the desired carboxy group. Thiol groups may be protected by disulphide formation, either with the thiol itself or with another thiol to form a mixed disulphide. The protecting groups may be removed at any convenient stage in the synthesis of the desired compound according to conventional techniques.

The following Examples illustrate the preparation of compounds according to the invention. Each of the compounds of the Examples demonstrates an affinity for the muscarinic receptor, having an $IC_{50}$ (concentration required to displace 50% of specific [$^3H$]-N-methylscopolamine binding from rat cortical membrane preparations) significantly lower than 100 μM. Penetrability into the central nervous system of compounds of this invention was assessed by a measurable displacement of radioligand binding using standard "ex-vivo" binding techniques (Ref: *J. Neurosurg.*, 1985, 63, 589–592).

In the Examples, all temperatures are in °C.; THF is tetrahydrofuran; and ether is diethyl ether.

EXAMPLE 1

3-[4-(2-Amino-1,3-thiazol)-yl]quinuclidine dihydrochloride.

(a) 3-Acetyl quinuclidine

Lithium hydroxide monohydrate (0.97 g, 0.023 mol) and 3-methoxycarbonylquinuclidine (4.0 g, 0.023 mol, prepared by the method of C. A. Grob and E. Renk, *Helv. Chim. Acta* (1954), 196, 1689) were heated under reflux in methanol (30 ml) for 24 hours. The solvent was evaporated and the residue dried in vacuo over phosphorus pentoxide to give 3-carboxyquinuclidine lithium salt (3.70 g) as a colourless solid.

A solution of methyl lithium (16.6 ml of a 1.4M solution in diethyl ether, 0.023 mol) was added dropwise to a cooled (0° C.), stirred suspension of 3-carboxyquinuclidine lithium salt (3.70 g, 0.023 mol) in dry tetrahydrofuran (50 ml) under an atmosphere of nitrogen.

After 18 hours at room temperature, water (50 ml) was added followed by diethyl ether (50 ml). The mixture was stirred vigorously for 15 minutes, the organic layer was separated and the aqueous re-extracted with diethyl ether (2×50 ml). The combined organics were dried (sodium sulphate), evaporated to dryness in vacuo to give 3-acetyl-quinuclidine as a colourless oil (1.21 g, 34%); ν max (liquid film) 1700 cm$^{-1}$ (C=O); m/e 153 (M+); δ (360 MHz, CDCl₃) 1.32–1.46 and 1.63–1.69 (each 2H, each m, 5 and 8CH₂); 2.16(3H, s, COCH₃); 2.16–2.19 (1H, m, 4CH); 2.60–2.65 (1H, m, 3CH); 2.68–2.90 (5H, m, 2CH, 6CH₂ and 7CH₂); 3.32 (1H, ddd, J=2,6,14 Hz, 2CH).

(b) 3-[4-(2-Amino-1,3-thiazol)-yl]quinuclidine dihydrochloride

A mixture of 3-acetylquinuclidine (0.45 g, 2.9 mmol), iodine (0.736 g, 2.9 mmol) and thiourea (0.447 g, 5.9 mmol) was heated on a steam bath for 6 hours, cooled then triturated with dry acetone. The acetone was decanted leaving a yellow solid which was partitioned between water (20 ml) and chloroform (20 ml) then basified with potassium carbonate. The organic layer was separated and the aqueous re-extracted with chloroform (2×20 ml). The combined organics were dried (potassium carbonate) then eaaporated to dryness in vacuo to give a pale yellow solid which was purified by column chromatography on neutral alumina [Merck Art 1077, Grade 3, 100 g] using dichloromethane/methanol (20:1). The title compound free base was obtained as a colourless solid (0.18 g, 30%) The dihydrochloride salt had mp 173°–175° C. (propan-2-ol/diethyl ether). (Found: C, 42.08; H, 6.86; N, 12.80; $C_{10}H_{15}N_3S.2HCl.0.4(CH_3)_2CHOH$ 0.75 H₂O requires C, 42.06; H, 6.84; N, 13.14%); m/e 209 (M+ of free base); δ (360 MHz, D₂O) 1.86–1.94 (2H, m, 5 and 8CH); 2.11(2H, dt, J=3, 8 Hz, 5 and 8CH); 2.38–2.40 (1H, m, 4CH); 3.26–3.52 (6H, m, 2CH, 3CH, 6CH₂ and 7CH₂); 3.70–3.78 (1H, m, 2CH); 6.72 (1H, s, S—CH=).

EXAMPLE 2

3-[4-(1,3-Thiazol)-yl]-quinuclidine hydrogen oxalate

A solution of sodium nitrite (0.77 g, 11 mmol) in water (2 ml) was added dropwise to a cooled (−15° C.), stirred solution of 3-[4-(2-amino-1,3-thiazol)-yl]quinuclidine (0.47 g, 2.2 mmol) in 50% hypophosphorus acid (10 ml), keeping the reaction mixture below −10° C. The mixture was allowed to warm to 6° C. and left standing at this temperature for 5 days. After dilution with water (30 ml) the solution was basified with potassium carbonate and extracted into dichloromethane (5×30 ml). The combined organics were washed with water (50 ml), dried (sodium sulphate) then evaporated in vacuo to give a yellow oil which was purified by column chromatography on neutral alumina [Merck Art 1077, Grade 3, 35 g] using dichloromethane/methanol (60:1) to give the title compound free base as a pale yellow oil (70 mg). The hydrogen oxalate salt had mp 122°–124° C. (acetone/methanol (10:1)). (Found: C, 46.46; H, 5.15; N, 7.91; $C_{10}H_{14}N_2S$. 1.75 $C_2H_2O_4$ requires C,46.08; H, 5.01; N, 7.96%) δ (360 MHz, D₂O) 1.83–1.90 and 2.07–2.20 (each 2H, each m, 5 and 8CH₂); 2.46–2.50 (1H, m, 4CH); 3.30–3.46 (4H, m); 3.61–3.66 (1H, m); 3.72–3.78 (1H, m) and 3.81–3.88 (1H, m) (2CH₂, 3CH, 6CH₂ and 7CH₂); 7.62 (1H, dd, J=1.8, 2 Hz, S—CH=C); 9.21 (1H, d, J=2 Hz, N=CH—S).

EXAMPLE 3

3-Hydroxy-3-[2-(4-methyl-1,3-oxazol)-yl]quinuclidine

A solution of n-butyllithium in hexane (1.6M, 50 ml, 80 mmol) was added dropwise over 30 min to a stirred solution of 4-methyloxazole (7.26 g, 87.5 mmol) in tetrahydrofuran (80 ml) under nitrogen, keeping the temperature below −65°. After a further 30 min at −70°, a solution of quinuclidin-3-one (9.10 g, 72.8 mmol) in tetrahydrofuran (20 ml) was added over 5 min. The mixture was kept at −70° for 2 h, then warmed to 25° overnight. Saturated ammonium chloride solution (50 ml ) was added, the organic layer separated, and the aqueous layer extracted three times with dichloromethane. The combined organic layers were dried over potassium carbonate and evaporated. The residue was dissolved in boiling ethyl acetate (250 ml), filtered and concentrated to 100 ml. The product crystallised on cooling as colourless prisms (4.98 g, 33%), m.p. 176°–177°. (Found: C, 63.25; H, 7.73; N, 13.40. $C_{11}H_{16}N_2O_2$ requires: C, 63.44; H, 7.74; N, 13.45%) ν max; 3200–2500 (br), 1600, 1550; m/e; 208 (M+); δ (CDCl$_3$); 1.32–1.57 (3H, m, 5CH and 8CH$_2$); 2.11–2.19 (2H, m, 4CH and 5CH); 2.17 (3H, d, J=1 Hz, CH$_3$); 2.76–2.88 (3H, m. 6CH$_2$ and 7CH); 2.94–3.01 (1H, m, 7CH); 2.96 (1H, dd, J=1 Hz and 14 Hz, 2CH); 3.78 (1H, dd, J=2 Hz and 14 Hz, 2CH); 7.35 (1H, q, J=1 Hz, oxazole-H).

EXAMPLE 4

3-[2-(4-Methyl-1,3-oxazol)-yl]quinuclidine hydrochloride a) 3-Chloro-3-[2-(4-methyl-1,3-oxazol-yl]quinuclidine

3-Hydroxy-3-[2-(4-methyl-1,3-oxazol)-yl]quinuclidine from Example 3 (1.50 g, 7.21 mmol) was added portionwise to stirred, ice-cooled thionyl chloride (15 ml), then the resulting solution heated under reflux for 1.5 h. The cooled solution was evaporated, aqueous potassium carbonate (2M, 50 ml) added and extracted three times with dichloromethane. Evaporation of the dried organic layers yielded the product as a brown oil (1.21 g, 74%), which was used immediately in the next reaction. m/e 228, 226 (M+ $^{37}$Cl. 35Cl); δ (CDCl$_3$); 1.22–1.30 (1H, m, 5CH); 1.54–1.67 (3H, m, 5CH and 8CH$_2$); 2.19 (3H, d, J=1 Hz, CH$_3$); 2.64–2.66 (1H, m, 4CH); 2.72–2.76 (2H, m) and 2.90–3.06 (2H, m, 6CH$_2$ and 7CH$_2$); 3.43 (1H, d, J=15 Hz, 2CH); 4.30 (1H, dd, J=2 Hz and 15Hz, 2CH); 7.39 (1H, q, J=1 Hz, oxazole H).

b) 3-[2-(4-Methyl-1,3-oxazol)-yl]quinuclidine hydrochloride

A solution of the foregoing chloroquinuclidine (1.21 g, 5.34 mmol), tributyltin hydride (2.0 ml, 7.4 mmol) and azobisisobutyronitrile (AIBN) (50 mg) was heated under reflux under a nitrogen atmosphere. Further portions of AIBN were added after 3 h and 5 h. After 8 h the cooled solution was partitioned between 2M hydrochloric acid and dichloromethane. The organic layer was extracted with more hydrochloric acid, the combined acid layers basified with solid potassium carbonate and extracted four times with dichloromethane. Chromatography of the residue from evaporation of the organic layers on alumina, eluting with dichloromethane/1% methanol yielded the title product (265 mg), which was converted to the hydrochloride (256 mg), m.p. 217°–219° (dec). (Found: C, 54.1; H, 7.3; N, 11.3; Cl 18.4; $C_{11}H_{16}N_2O.1.4$ HCl requires C, 54.3; H, 7.2; N, 11.5; Cl, 20.4%) m/e; 192 (M+); δ (D$_2$O); 1.78–1.92 (3H, m, 5CH and 8CH$_2$); 2.08–2.13 (1H, m, 5CH); 2.12 (3H, d, J=1Hz, CH$_3$); 2.55–2.58 (1H, m, 4CH); 3.28–3.41 (4H, m, 6CH$_2$ and 7CH2); 3.64–3.76 (3H, m, 2CH$_2$ and 3CH); 7.58 (1H, q, J=1Hz, oxazole H).

EXAMPLE 5

(+)-3-[2-(4-Methyl-1,3-oxazol)-yl]quinuclidine hemi dibenzoyl tartrate

A solution of 3-[2-(4-methyl-1,3-oxazol)-yl]quinuclidine from Example 4 (679 mg, 3.54 mmol) in ethanol (1.0 ml) was treated with (+)-O,O'dibenzoyl tartaric acid (317 mg, 0.843 mmol) in ethanol (1.5 ml). The resulting solution was left at 4° for 24 h, and the crystals formed collected and washed with cold ethanol (382 mg). This was recrystallised from ethanol to yield the title compound (182 mg), m.p. 164°–165°, [α]$_D$+67.5°. A portion of this material (10 mg), was converted to the borane complex by first liberating the free-base, then treating with excess borane in tetrahydrofuran at 0° followed by aqueous work-up, and extraction into dichloromethane. The borane complex isolated from the organic layer was analysed by high performance liquid chromatography on a cyclobond I-acetylated column, in 40% methanol-0.4% triethylamine acetate, pH 4.0, which indicated an enantiomeric excess of 72%. (Found: C, 64.14; H, 6.23; N, 7.42; $C_{11}H_{16}N_2O$. 0.5 $C_{18}H_{14}O_8.0.2H_2O$ requires: C, 64.06; H, 6.29; N, 7.47%); m/e 192 (M+); δ (360 MHz, D$_2$O); 1.76–1.90 (2H, m, 5CH and 8CH); 2.04–2.16 (2H, m, 5CH and 8CH); 2.14 (3H, s, oxazole-CH$_3$); 2.54–2.58 (1H, m, 4CH); 3.29–3.43 (4H, m, 6C$\overline{H}_2$ and 7CH$_2$); 3.63–3.76 (3H, m, 2CH$_2$ and 3CH); 5.72 (1H, s, CHCO$_2$H); 7.53–7.60 (3H, m, oxazole CH+phenyl 3CH $\overline{\text{and}}$ 5CH); 7.71 (1H, t, J=6 Hz, phenyl 4CH); 8.12 (2H, d, J=6 Hz, phenyl 2CH and 6CH).

EXAMPLE 6

(−)-3-[2-(4-Methyl-1,3-oxazol)-yl]quinuclidine hemi dibenzoyl tartrate

The mother liquors from the initial crystallisation in Example 5 were basified with aqueous potassium carbonate and extracted with dichloromethane. The organic extracts were dried over magnesium sulphate and evaporated to yield the free base (424 mg, 2.21 mmol). This material in ethanol (0.6 ml) was treated with (−)O,O,' dibenzoyl tartaric acid (313 mg, 0.832 mmol) in ethanol (1.5 ml). The resulting solution was left at 4° for 18 h and the crystals collected (286 mg). This was recrystallised from ethanol to give the title compound (81 mg), m.p. 162.5°–164.5°, [α$_D$] −66.2°. A portion of this material (10 mg) was converted to the borane complex and analysed as described in Example 5, indicating an enantiomeric excess of 92%. (Found: C, 63.84; H, 6.26; N, 7.21; $C_{11}H_{16}N_2O.0.5$ $C_{18}H_{14}O_8$. 0.25H$_2$O requires C, 63.90; H, 6.30; N, 7.45%); m/e 192 (M+); δ (360 MHz, D$_2$O); 1.76–1.88 (2H, m, 5CH and 8CH); 2.06–2.16 (2H, m, 5CH and 8CH); 2.13 (3H, d, J=1 Hz, oxazole CH$_3$); 2.54–2.58 (1H, m, 4CH); 3.30–3.43 (4H, m, 6CH$_2$ and 7CH$_2$); 3.63–3.76 (3H, m, 2CH$_2$ and 3CH); 5.72 (1H, s, CHCO$_2$H); 7.53–7.60 (3H, m, oxazole CH+phenyl 3$\overline{\text{CH}}$ and 5CH); 7.71 (1H, t, J=6 Hz, phenyl 4CH); 8.12 (2H, d, J=6 Hz, phenyl 2CH and 6CH).

EXAMPLE 7

3-Hydroxy-3-[2-(1,3-oxazol)-yl]quinuclidine

A solution of n-butyllithium in hexane (2.5M, 31 ml, 77.5 mmol) was added dropwise over 20 min to a stirred solution of oxazole (5.89 g, 85.4 mmol) in tetrahydrofuran (80 ml) under nitrogen, keeping the temperature below −55°. After a further 30 min at −70° a solution of quinuclidin-3-one (8.9 g, 71.2 mmol) in tetrahydrofuran (23 ml) was added. The mixture was allowed to warm slowly to 20° overnight. Saturated ammonium chloride solution (50 ml) was added, the organic layer separated and the aqueous layer extracted three times with dichloromethane. The combined organic layers were dried over potassium carbonate and evaporated. The residue was extracted with boiling ethyl acetate (250 ml), filtered and concentrated to 80 ml. On cooling the title compound was obtained as colourless needles (2.58 g, 19%), m.p. 196°–198°. (Found: C, 61.71; H, 7.32; N, 14.26; $C_{10}H_{14}N_2O_2$ requires: C, 61.84; H, 7.27; N, 14.42%); $\nu$ max 3100–2500 (br), 1560; m/e (CI) 195 (M+H+); δ (360 MHz, CDCl$_3$) 1.27–1.37 (1H, m, 8CH); 1.45–1.57 (2H, m, 5CH and 8CH); 1.60–1.90 (1H, br, OH); 2.12–2.22 (2H, m, 4CH and 5CH); 2.78–2.92 (3H, m, 6CH and 7CH$_2$); 2.96–3.04 (1H, m, 6CH); 3.01 (1H, dd, J=1 Hz and 14.5 Hz, 2CH); 3.84 (1H, dd, J=2 Hz and 14.5 Hz, 2CH); 7.10 (1H, d, J=1 Hz, oxazole 4CH); 7.66 (1H, d, J=1 Hz, oxazole 5CH).

EXAMPLE 8

3-Hydroxy-3-[2-(4-ethyl-1,3-oxazol)-yl]quinuclidine a) Ethyl 4-ethyloxazole-5-carboxylate

Ethyl 2-chloro-3-oxopentanoate (29.2 g, 0.164 mol) prepared by the method of E. A. Falco, P. B. Russell and G. H. Hitchings, *J. Am. Chem. Soc*, 1951, 73, 3753, and ammonium formate (60 g, 0.95 mol) were heated in 100% formic acid (180 ml) under reflux for 5 h. The cooled mixture was diluted with water (300 ml) and diethyl ether (200 ml), then neutralised with aqueous sodium hydroxide (5M). The layers were separated and the aqueous layer extracted with more ether (4×200 ml). The combined ether layers were dried over magnesium sulphate and the solvent removed by distillation at atmospheric pressure. Vacuum distillation of the residue yielded the desired oxazole (11.2 g, 40%) b.p. 100°–106° (7 mm). This was contaminated with starting material. An analytical sample, obtained by extracting into 5M sulphuric acid, had b.p. 97°–98° (7 mm). (Found C, 56.64; H, 6.63; N, 8.24; $C_8H_{11}NO_3$ requires: C, 56.80; H, 6.55; N, 6.28%); m/e 169 (M+); δ (360 MHz, CDCl$_3$) 1.27 (3H, J=7.5 Hz, ArCH$_2$CH$_3$); 1.40 (3H, t, J=7 Hz, CO$_2$CH$_2$CH$_3$); 2.91 (2H, q, J=7.5 Hz, arCH$_2$CH$_3$); 4.40 (2H, q, J=7 Hz, CO$_2$CH$_2$CH$_3$); 7.89 (1H, s, ArH).

b) 4-Ethyloxazole

A solution of the foregoing oxazole ester (23.2 g, 0.14 mol) in ethanol (25 ml) and aqueous sodium hydroxide (2M, 75 ml, 0.15 mol) was stirred at 22° for 2 h. The solvent was then evaporated and the residue dried under vacuum over phosphorus pentoxide. A suspension of the sodium salt in quinoline (42 ml) containing quinoline sulphate (26.7 g, 0.075 mol) was heated in an oil bath at 230°. The oxazole was collected at 92°–110° and dried over KOH pellets and redistilled, b.p. 98°–102°, yield 3.73 g (27%). (Found: C, 58.73; H, 7.49; N, 13.41; $C_5H_7NO$. 0.3H$_2$O requires C, 58.58; H 7.47; N 13.66%); δ (60 MHz, CDCl$_3$) 1.25 (3H, t, J=7 Hz, CH$_2$CH$_3$); 2.55 (2H, q, J=7 Hz, CH$_2$CH$_3$); 7.25 (1H, s, 5CH); 7.70 (1H, s, 2CH).

c) 3-Hydroxy-3-[2-(4-ethyl-1,3-oxazol)-yl]quinuclidine

A solution of n-butyllithium in hexane (2.5M, 14 ml, 35 mmol) was added dropwise over 20 min to a stirred solution of the foregoing 4-ethyloxazole (3.73 g, 38.5 mmol) in dry tetrahydrofuran (40 ml) under nitrogen at −75°. After a further 30 min, a solution of quinuclidin-3-one (4.01 g, 32.1 mmol) in tetrahydrofuran (10 ml) was added and the mixture allowed to warm slowly to 20° overnight. Saturated aqueous ammonium chloride (50 ml) was added and the layers separated. The aqueous layer was extracted with dichloromethane (4×50 ml) and the combined organic layers dried over magnesium sulphate and evaporated. Column chromatography of the residue on neutral alumina, grade III, in dichloromethane/methanol (99:1) yielded the title compound (693 mg, 10%), m.p. 118°–120° (Found: C, 64.10; H, 8.03; N, 12.27; $C_{12}H_{18}N_2O_2$.0.1H$_2$O requires C, 64.32; H, 8.19; N, 12.50%); m/e 222 (M+); δ (360 MHz, CDCl$_3$) 1.22 (3H, t, J=7.5 Hz, CH$_2$CH$_3$); 1.32–1.56 (3H, m, 5CH and 8CH$_2$); 1.90–2.10 (1H, br, OH); 2.12–2.20 (2H, m, 4CH and 5CH); 2.55 (2H, dq, J=1 Hz and 7.5 Hz, CH$_2$CH$_3$); 2.73–2.89 (3H, m, 6CH$_2$ and 7CH); 2.94–2.99 (1H, m, 7CH); 2.96 (1H, dd, J=2 Hz and 14 Hz, 2CH); 3.78 (1H, dd, J=2 Hz and 14 Hz, 2CH); 7.33 (1H, t, J=1 Hz, oxazole CH).

EXAMPLE 9

3-[2-(4-Ethyl-1,3-oxazol)-yl]quinuclidine hydrogen fumarate a) 3-Chloro-3-[2-(4-ethyl-1,3-oxazol)-yl)quinuclidine

3-Hydroxy-3-[2-(4-ethyl-1,3-oxazol)-yl]quinuclidine from Example 8 (640 mg, 2.88 mmol) was added to ice cold thionyl chloride (6 ml) and the resulting solution heated under reflux for 1.5 h. The cooled solution was evaporated, residual thionyl chloride removed using a toluene azeotrope, and the residue partitioned between aqueous potassium carbonate (2M, 50 ml) and dichloromethane (100 ml). The organic layer was dried over magnesium sulphate to give the 3 chloroquinuclidine (718 mg) δ (360 MHz, CDCl$_3$) 1.24 (3H, t, J=7.5 Hz, CH$_2$CH$_3$); 1.56–1.63 (3H, m, 5CH and 8CH$_2$); 2.24–2.29 (1H, m, 5CH); 2.57 (2H, dq, J=1 Hz and 7.5 Hz CH$_2$CH$_3$); 2.64–2.67 (1H, m, 4CH); 2.72–2.77 (2H, m, 6CH and 7CH); 2.92–2.97 (1H, m 6CH); 3.02–3.07 (1H m, 7CH); 3.44 (1H, d, J=15 Hz, 2CH); 4.32 (1H, dd, J=2 Hz and 15 Hz, 2CH); 7.37 (1H, t, J=1 Hz, oxazole H).

b) 3-[2-(4-Ethyl-1,3-oxazol)-yl]quinuclidine hydrogen fumarate

A solution of the foregoing chloroquinuclidine (710 mg, 2.85 mmol), tributyltin hydride (1.1 ml, 4.1 mmol) and azobisisobutyronitrile (AIBN) (10 mgs) in dry tetrahydrofuran (12 ml) under nitrogen was stirred and heated under reflux. After 1.5 h, a further portion of AIBN was added and heating continued for a further 4 h. The coo-led solution was partitioned between 2M hydrochloric acid (30 ml) and dichloromethane (40 ml). The aqueous layer was basified with solid sodium carbonate and extracted with dichloromethane (4×60 ml). The combined organic layers were dried over magnesium sulphate, evaporated and the residue purified by column chromatography on neutral alumina, grade III, in dichloromethane/methanol (99:1) to yield the title compound free base (368 mg, 63%), which was converted to the hydrogen fumarate and recrystallised from propan-2-ol to yield the title compound (273 mg). m.p. 108°–113° (Found: C, 58.75; H, 6.84; N, 8.60; $C_{12}H_{18}N_2O.1.1 C_4H_4O_4$ requires C, 58.98; H, 6.76; N, 8.39%); m/e 206 (M+); δ (360 MHz, D$_2$O) 1.17 (3H, t, J=7.5 Hz, CH$_2$CH$_3$); 1.78–1.89 (2H, m, 8CH$_2$); 2.07–2.15 (2H, m, 5CH$_2$); 2.51 (2H, dq, J=1 Hz and 7.5 Hz, CH$_2$CH$_3$); 2.54–2.58 (1H, m, 4CH); 3.23–3.41 (4H, m, 6CH$_2$ and 7CH$_2$); 3.67–3.78 (3H, m, 2CH$_2$ and 3CH); 6.66 (2.2H, s, HO$_2$C CH=CHCO$_2$H); 7.59 (1H, t, J=1 Hz, oxazole H).

EXAMPLE 10

3-Hydroxy-3-[2-(4-methyl-1,3-thiazol)-yl]quinuclidine

A solution of n-butyllithium in hexane (1.6M, 25 ml, 40 mmol) was added to a stirred solution of 4-methylthiazole in tetrahydrofuran (50 ml) under nitrogen, keeping the temperature below −60°. After 1 h at −60° a solution of quinuclidin-3-one (4.55 g 36.4 mmol) in tetrahydrofuran was added dropwise, maintaining the same temperature. After a further 0.5 h at −60°, the mixture was allowed to warm slowly to 20°. Methanol (10 ml) was added and the solvent evaporated. The residue was partitioned between dichloromethane and water and the organic layer dried over sodium sulphate, and evaporated. Recrystallisation of the solid residue from ethyl acetate yielded the title compound (4.2 g, 51%), m.p. 183°-186°. (Found: C, 58.9; H, 7.3; N, 12.3; $C_{11}H_{16}N_2OS$ requires: C, 58.9; H, 7.2; N, 12.5%). $\nu$ max (Nujol) 3200-2500 (br), 1530 cm$^{-1}$; m/e 224 (M$^+$); $\delta$ (360 MHz, CDCl$_3$) 1.38-1.50 (2H, m, 8CH$_2$); 1.56-1.65 (1H, m, 5CH); 2.04-2.07 (1H, m, 4CH); 2.15-2.24 (1H, m, 5CH); 2.42 (3H, d, J=1 Hz, Ar CH$_3$); 2.67-2.93 (4H, m, 6CH$_2$ and 7CH$_2$); 2.97 (1H, dd, J=2 Hz and 14 Hz, 2CH); 3.71 (1H, dd, J=2 Hz and 14 Hz, 2CH); 4.06-4.26 (1H, br, OH); 6.82 (1H, q, J=1 Hz, SC$\underline{H}$=C).

EXAMPLE 11

3-[2-(4-Methyl-1,3-thiazol)-yl]-1-azabicyclo [2.2.2]oct-2-ene dihydrochloride 3-Hydroxy-3-[2-(4-methyl-1,3-thiazol)-yl]quinuclidine from Example 10 (1.0 g, 4.5 mmol) was added to stirred thionyl chloride (10 ml) at 20° and the solution heated to reflux for 1.5 h. The cooled solution was evaporated and last traces of thionyl chloride removed using a toluene azeotrope. The residue was dissolved in boiling ethanol, and cooled, whereupon the title compound crystallised (225 mg, 18%) m.p. 179°-182° (Found: C, 47.0; H, 5.7; N, 10.0; $C_{11}H_{14}N_2S.2HCl$ requires: C, 47.3; H, 5.8; N, 10.0%). $\delta$ max 2100-2500 (br), 1580; m/e 206 (M$^+$); $\delta$ (360 MHz, D$_2$O) 1.88-1.99 (2H, m, 5CH and 8CH); 2.19-2.28 (2H, m, 5CH and 8CH); 2.52 (3H, d, J=1 Hz, CH$_3$); 3.24-3.33 (2H, m, 6CH and 7CH); 3.68-3.77 (3H, m, 4CH, 6CH and 7CH); 7.48 (1H, q, J=1 Hz, SC$\underline{H}$=C); 7.52 (1H, d, J=1 Hz, NC$\underline{H}$=C).

EXAMPLE 12

3-[2-(4-Methyl-1,3-thiazol)-yl]quinuclidine dihydrochloride

3-[2-(4-Methyl-1,3-thiazol)-yl]-1-azabicyclo [2.2.2]oct-2-ene dihydrochloride from Example 11 (150 mg, 0.537 mmol) was hydrogenated over sulphided platinum (150 mg) in methanol (25 ml) at 40 p.s.i. for 18 h. The catalyst was removed by filtration through Hyflo and the solvent evaporated to dryness to yield the title compound as an amorphous hygroscopic solid (125 mg, 83%); m/e 208.1036; $C_{11}H_{16}N_2S$ requires 208.1034; $\delta$ (360 MHz, D$_2$O) 1.84-1.96 (2H, m, 8CH$_2$); 2.07-2.15 (2H, m, 5CH$_2$); 2.40 (3H, s, CH$_3$); 2.49-2.55 (1H, m, 4CH); 3.27-3.48 (4H, m, 6CH$_2$ and 7CH$_2$); 3.74-3.94 (3H, m, 2CH$_2$ and 3CH); 7.15 (1H, s, SC$\underline{H}$=C).

EXAMPLE 13

3-[2-(5-Methyl-1,3-oxazol)-yl]quinuclidine hydrogen fumarate

Quinuclidine-3-carboxylic acid hydrochloride, prepared by the method of C. A. Grob and E. Renk, Helv. Chim. Acta, 1954, 37, 1689 (4.88 g, 25.5 mmol) was added to stirred thionyl chloride (60 ml) with ice cooling, and the resulting solution was heated to reflux for 2.5 h. The cooled mixture was evaporated and last traces of thionyl chloride removed using a toluene azeotrope. The residue was suspended in dry dichloromethane (50 ml) under nitrogen, propargyl amine (3.5 ml, 51 mmol) and triethyl amine (6.0 ml, 43 mmol) added and the mixture stirred at 20° for 16 h. Aqueous potassium carbonate (2M, 30 ml) was added and solution extracted with dichloromethane (4×50 ml). The combined extracts were dried over potassium carbonate and evaporated to yield the crude propargyl amide (2.8 g). This material was dissolved in acetic acid (45 ml), mercuric acetate (262 mg, 0.82 mmol) added and the mixture heated under reflux for 3 h. The cooled solution was evaporated and aqueous potassium carbonate added. The product was extracted into dichloromethane (4×50 ml), dried over potassium carbonate and evaporated to give a gum which was purified by column chromatography on neutral alumina, grade III, eluting with dichloromethane/methanol (99:1) to give the title compound free base as a colourless gum (748 mg, 16% overall). The hydrogen fumarate salt had m.p. 123°-125° (propan-2-ol/diethyl ether). (Found: C, 57.85; H, 6.52; N, 8.95; $C_{11}H_{16}N_2O$. 1.1 $C_4H_4O_4$ requires: C, 57 81; H, 6.43; N, 8.76%); m/e 192 (M$^+$); $\delta$ (360 MHz, D$_2$O) 1.78-1.88 (2H, m, 8CH$_2$); 2.07-2.15 (2H, m, 5CH$_2$); 2.29 (3H, d, J=1 Hz, CH$_3$); 2.54-2.57 (1H, m, 4CH); 3.31-3.42 (4H, m, 6CH$_2$ and 7CH$_2$); 3.62-3.76 (3H, m, 2CH$_2$ and 3CH); 6.66 (2.2H, s, HO$_2$CCH=CHCO$_2$H); 6.76 (1H, q, J=1 Hz, NC$\underline{H}$=CO).

EXAMPLE 14

1-Methyl-3-[2-(5-methyl-1,3-oxazol)-yl]piperidine hydrogen oxalate a) 1-Methyl-N-(3-propynyl)piperidine-3-carboxamide 1-Methyl piperidine-3-carboxylic acid hydrochloride (21 g, 0.12 mol) was added to stirred thionyl chloride (50 ml) at 20° and the mixture heated under reflux for 15 min. The cooled solution was evaporated and residual thionyl chloride removed using a toluene azeotrope. This material was suspended in dry tetrahydrofuran (250 ml) under nitrogen, cooled to 0° and treated with propargyl amine (6.45 g, 0.12 mol) and triethylamine (12.1 g, 0.12 mol). The cooling bath was removed and the mixture stirred at 20° for 18 h. The solvent was evaporated, the residue dissolved in water, basified to pH 10 with potassium carbonate and extracted three times with dichloromethane. The extracts were dried over sodium sulphate and evaporated to yield the propargyl amide (17 g, 81%). which was characterised as the hydrogen oxalate salt, m.p. 150°. (Found: C, 53.0; H, 6.8; N, 10.4; $C_{10}H_{16}N_2O$. $C_2H_2O_4$ requires: C, 53.3; H, 6.7; N, 10.0%); $\delta$ max (Nujol) 3250, 3190, 3080, 2120(w) 1640; m/e 180 (M$^+$); $\delta$ (360 MHz. D$_2$O) 1.54-1.66 (1H, m, 5CH); 1.75-2.10 (4H, m, 4CH$_2$, 5CH and NH); 2.59-2.62 (1H, m, C≡CH); 2.73-2.84 (1H, m, 3CH); 2.89 (3H, s, NCH$_3$); 2.91-3.07 (2H, m, 2CH and 6CH); 3.42-3.64 (2H, m, 2CH and 6CH); 3.95-3.98 (2H, m, HNCH$_2$C≡).

b) 1-Methyl-3-[2-(5-methyl-1,3-oxazol)-yl]piperidine hydrogen oxalate

A solution of the foregoing propargyl amide free base (1.8 g, 10 mmol) in acetic acid (20 ml) containing mercuric acetate (30 mg, 0.1 mmol) was heated under reflux for 5 h, cooled, and evaporated. The residue was partitioned between dichloromethane and saturated potassium carbonate, the organic layer dried over sodium sulphate and evaporated. The resulting oil was purified by chromatography on neutral alumina, grade III in ethyl acetate. The product was treated with ethereal oxalic acid and crystallised from propan-2-ol to yield the title compound (680 mg, 25%). m.p. 101-103 (Found: C, 51.1; H, 6.4; N. 9.5; $C_{10}H_{16}N_2O.C_2H_2O_4.0.67 H_2$) requires: C, 51.1; H, 6.8; N, 9.9%). δ (360 MHz, DMSO) 1.53–1.65 (1H, m, 5CH); 1.76–1.91 (2H, m, 5CH and 4CH); 2.05–2.11 (1H, m, 4CH); 2.27 (3H, d, J=1 Hz, oxazole $CH_3$); 2.76 (3H, s, $NCH_3$); 2.86–2.95 (1H, m, 6CH); 3.09 (1H, t, J=12 Hz, 2CH); 3.28–3.36 (2H, m, 3CH and 6CH); 3.61 (1H, d, J=12 Hz, 2CH); 6.77 (1H, q, J=1 Hz, oxazole CH).

EXAMPLE 15

1-Methyl-3-[2-(5-methyl-1,3-oxazol)-yl]-1,2,5,6-tetrahydropyridine sesquifumarate 1-Methyl-1,2,5,6-tetrahydropyridine carboxylic acid hydrochloride, obtained by hydrolysis of arecoline with 5M hydrochloric acid (5.07 g, 36 mmol) was added to stirred thionyl chloride (50 ml) at 20° and the resulting solution heated under reflux for 2.5 h. The cooled solution was evaporated and residual thionyl chloride removed using a toluene azeotrope. The residue was suspended in dry dichloromethane (50 ml) under nitrogen, cooled in ice and treated with propargyl amine (3.6 ml, 53 mmol). The cooling bath was removed and the mixture stirred at 20° for 18 h. Aqueous potassium carbonate (2M, 40 ml) was added and the product extracted with dichloromethane (4×60 ml). The extracts were dried over magnesium sulphate and evaporated to give the crude propargyl amide (5.49 g). This material was dissolved in acetic acid (70 ml), mercuric acetate (0.53 g, 1.7 mmol) added, and the mixture heated under reflux for 3 h. The cooled solution was evaporated to dryness, aqueous potassium carbonate (50 ml) added and extracted with dichloromethane (3×50 ml). The extracts were dried over magnesium sulphate and evaporated to yield a dark gum which was purified by column chromatography on silica in dichloromethane/methanol (95:5) to give the title compound free base (730 mg, 11% overall), which was treated with fumaric acid (478 mg, 4.12 mmol) and recrystallised from ethanol to give the title compound (385 mg), m.p. 145°-147°. (Found: C, 54.45; H, 5.72; N, 7.94; $C_{10}H_{14}N_2O.1.5 C_4H_4O_4$ requires: C, 54.54; H, 5.72; N, 7.95%; m/e 178 (M+); δ (360 MHz, $D_2O$) 2.32 (3H, d, J=1 Hz, oxazole $CH_3$); 2.68–2.81 (2H, m, 5$CH_2$); 3.05 (3H, s, $NCH_3$); 3.26–3.34 (1H, m, 6CH); 3.62–3.67 (1H, m, 6CH); 3.95 (1H, dq, J=2 Hz and 16 Hz, 2CH); 4.32 (1H, d, J=16 Hz, 2CH); 6.72 (3H, s, $HO_2CCH=CHCO_2H$); 6.82 (1H, q, J=1 Hz, $NC\underline{H}=C$); 6.88–6.90 (1$\overline{H}$, m, 4CH).

EXAMPLE 16

3-[2-(5-Methyl-1,3-oxazol)-yl]-1,2,5,6-tetrahydropyridine hydrochloride a)
1-Ethenyloxycarbonyl-3-[2-(5-methyl-1,3-oxazol)-yl]-1,2,5,6-tetrahydropyridine To a stirred solution of 1-methyl-3-[2-(5-methyl-1,3-oxazol)-yl]-1,2,5,6-tetrahydropyridine (550 mg, 3.09 mmol), from Example 15, in 1,2-dichloroethane (5 ml) at −5° was added vinyl chloroformate (0.34 ml, 3.7 mmol). After 10 min, the solution was heated to reflux for 1.5 h, then cooled, diluted with dichloromethane (20 ml) and washed in turn with 0.5M hydrochloric acid (10 ml) and saturated sodium hydrogen carbonate (10 ml). The organic layer was dried over magnesium sulphate, evaporated and the residue in dichloromethane/ethyl acetate (95:5) filtered through a plug of silica gel to remove baseline material. Evaporation of the eluate yielded the title carbamate as an oil (450 mg, 62%). m/e 234 (M+); δ (360 MHz, $CDCl_3$) 2.33 (3H, s, $CH_3$); 2.38–2.42 (2H, m, 5$CH_2$); 3.62–3.68 (2H, m, 6$CH_2$); 4.42–4.47 (2H, m, 2$CH_2$); 4.47 (1H, dd, J=2 Hz and 6 Hz, $CO_2CH=CH$, trans to O); 4.85 (1H, d, J=14 Hz, $CO_2CH=CH$, cis to O); 6.74 (1H, s, oxazole H); 6.74–6.78 (1$\overline{H}$, m, 4CH); 7.24 (1H, dd, J=6 Hz and 14 Hz, $CO_2C\underline{H}=C$).

b)
3-[2-(5-Methyl-1,3-oxazol)-yl]-1,2,5,6-tetrahydropyridine hydrochloride

A solution of the foregoing vinyl carbamate (220 mg, 0.94 mmol) in methanolic hydrogen chloride (10 ml) was stirred at 20° for 36 h and evaporated to dryness. The residue was triturated with diethyl ether and recrystallised from propan-2-ol to yield the title compound, (132 mg, 67%) m.p. 169°-171 ° (Found: C, 52.74; H, 6.62; N. 13.18; $C_9H_{12}N_2O$. 1.15 HCl.0.04 $C_3H_8O$ requires: C, 52.53; H, 6.51; N, 13.43%); m/e 164 (M+); δ (360 MHz, $D_2O$) 2.32 (3H, d, J=1 Hz, $CH_3$); 2.62–2.68 (2H, m, 5$CH_2$); 3.42 (2H, t, J=6 Hz, 6$CH_2$); 4.06–4.09 (2H, m, 2$CH_2$); 6.82 (1H, q, J=1 Hz oxazole CH); 6.88–6.92 (2H, m, 4CH).

EXAMPLE 17

1-Methyl-3-[4-(2-methyl-1,3-thiazol)-yl]-1,2,5,6-tetrahydropyridine hemifumarate a) 1-Methyl-3-[4-(2-methyl-1,3,-thiazol)-yl]pyridinium iodide 3-[4-(2-Methyl-1,3-thiazol)-yl]pyridine hydrobromide (29.2 g, 11.4 mmol), prepared by the method of D. J. Brown et al, Aust. J. Chem., 1980, 33, 2291, was partitioned between dichloromethane and aqueous potassium carbonate, and the organic layer dried over magnesium sulphate and evaporated to yield the free base (20.1 g, 100%). This material was dissolved in acetone (100 ml) with warming, cooled to 20° and methyl iodide (8.3 ml, 13.3 mmol) added with stirring. After 3 days at 20° the precipitate was collected, washed with acetone and ether and dried to yield the title compound (34.3 g, 95%), m.p. 148°-149° (Found: C, 37.58; H, 3.50; N, 8.78; S, 10.04; $C_{10}H_{11}IN_2S$ requires: C, 37.75; H, 3.48; N, 8.80; S, 10.08%); m/e 191 (M+); δ (360 MHz, $D_2O$) 2.81 (3H, s, $SCCH_3$); 4.67 (3H, s, $NCH_3$); 8.07 (1H, s, SCH); 8.11 (1H, dd, J=7 Hz and 8 Hz, 5CH); 8.73 (1H, d, J=7 Hz, 4CH); 8.88 (1H, d, J=8 Hz, 6CH); 9.26 (1H, s, 2CH).

b)
1-Methyl-3-[4-(2-methyl-1,3-thiazol)-yl]-1,2,5,6-tetrahydropyridine hemifumarate A stirred solution of the foregoing pyridinium salt (19.1 g, 60.1 mmol) in water (150 ml) and ethanol (150 ml) was cooled in ice and sodium borohydride (2.30 g, 60 mmol) added. After the initial reaction, the cooling bath was removed and stirring continued for 2 h at 20°. Excess borohydride was destroyed by adding concentrated hydrochloric acid dropwise, then the solution was basified with aqueous potassium carbonate and ethyl acetate (300 ml) added. The layers were separated and the aqueous layer extracted with dichloromethane (3×200 ml). The combined organic layers were dried over magnesium sulphate, evaporated and purified by column chromatography on silica in dichloromethane/methanol (95:5) to give the free base of the title compound (9.75 g, 84%). A portion of this material (1.5 g, 8.14 mmol) was treated with fumaric acid (0.425 g, 3.66 mmol) in methanol and concentrated to yield the title hemifumarate (1.53 g, 76% recovery), m.p. 139°-141° (Found: C, 57.03; H, 6.39; N, 11.14; $C_{10}H_{14}N_2S$. 0.5 $C_4H_4O_4$ requires: C, 57.12; H, 6.39; N, 11.10%); m/e 194 (M+); δ (360 MHz, DMSO) 2.28–2.33 (2H, m, 5CH$_2$); 2.41 (3H, s, SCCH$_3$); 2.57–2.61 (2H, m, 6CH$_2$); 3.30–3.32 (2H, m, 2CH$_2$); 6.54 (1H, s, SCH); 6.54–6.57 (1H, m, 4CH); 7.29 (1H, s, HO$_2$CC$\underline{H}$=C$\underline{H}$CO$_2$H).

EXAMPLE 18

3-[4-(2-Methyl-1,3-thiazol)-yl]-1,2,5,6-tetrahydropyridine dihydrochloride a)

1-Ethenyloxycarbonyl-3-[4-(2-methyl-1,3-thiazol)-yl]-1,2,5,6-tetrahydropyridine

A solution of 1-methyl-3-[4-(2-methyl-1,3-thiazol)-yl]-1,2,5,6-tetrahydropyridine (7.31 g, 37.7 mmol), from Example 17, in 1,2-dichloroethane (50 ml), was treated with vinyl chloroformate (4.3 ml, 47.1 mmol) exactly as described in Example 16 to yield the title compound as a solid (7.10 g, 75%). m/e (CI) 251 (M+H+); δ (CDCl$_3$) 2.35–2.41 (2H, m, 5CH$_2$); 2.71 (3H, s, CH$_3$); 2.62–2.68 (2H, m, 6CH$_2$); 4.36 (2H, brd, J=12 Hz, 2CH$_2$); 4.48 (1H, dd, J=1.5 Hz and 6 Hz, CO$_2$CH=C$\underline{H}$, trans to O); 4.82 (1H, dd, J=1.5 Hz and 14 Hz, CO$_2$C$\underline{H}$=CH, cis to O); 6.75–6.82 (1H, m, 4CH); 6.89 (1H, s, thiazole CH); 7.26 (1H, dd, J=6 Hz and 14 Hz, CO$_2$C$\underline{H}$=CH$_2$).

b)

3-[4-(2-Methyl-1,3-thiazol)-yl]-1,2,5,6-tetrahydropyridine dihydrochloride

A suspension of the foregoing vinyl carbamate (7.76 g, 31.0 mmol) in methanolic hydrogen chloride was stirred at 20° for 36 h and evaporated to dryness. The residue was triturated with diethyl ether and recrystallised from methanol to yield the title compound as fine needles (5.89 g, 75%), m.p. 227°–230° (dec). (Found: C, 42.3; H, 5.6; N, 11.0; Cl, 28.0; $C_9H_{12}N_2S$.2HCl requires: C, 42.7; H, 5.6; N, 11.1; Cl, 28.0%); m/e 180 (M+); δ (360 MHz, D$_2$O) 2.62–2.68 (2H, m, 5CH$_2$); 2.88 (3H, s, CH$_3$); 3.43 (2H, t, J=6 Hz, 6CH$_2$); 4.08–4.10 (2H, m, 2CH$_2$); 6.70–6.72 (1H, m, 4CH); 7.54 (1H, s, thiazole CH).

EXAMPLE 19

1-Methyl-3-[4-(2-methyl-1,3-oxazol)-yl]-1,2,5,6-tetrahydropyridine hydrogen fumarate a) 3-[4-(2-Methyl-1,3-oxazol)-yl]-pyridine A solution of 3-(bromoacetyl)pyridine hydrobromide, (28.1 g, 0.10 mol), prepared by the method of A. Dornow, H. Machens, K. Bruncken, Chem. Ber., 1951, 84, 148, and acetamide (12 g, 0.20 mol) in acetic acid (100 ml) was heated under reflux for 22 h, cooled, and the solvent evaporated. The residue was dissolved in water (100 ml), dichloromethane (100 ml) added and the solution basified with aqueous potassium carbonate. The mixture was filtered through Hyflo to remove a considerable amount of tar, and the layers separated. The aqueous layer was extracted with more dichloromethane (3×100 ml) and the combined organic layers dried over magnesium sulphate and evaporated. Column chromatography of the residue on silica in dichloromethane/methanol (98:2), increasing to (95:5) yielded the desired oxazole as the second-eluted component as a pale orange solid (2.75 g, 17%). An analytical sample was recrystallised from ether, m.p. 84°–86° (Found: C, 67.40; H, 5.09; N, 17.41; $C_9H_8N_2O$ requires: C, 67.49; H, 5.03; N, 17.49%); m/e 160 (M+); δ (360 MHz, CDCl$_3$) 2.54 (3H, s, CH$_3$); 7.33 (1H, dd, J=5 Hz and 8 Hz, 5CH); 7.89 (1H, s, oxazole H); 8.01 (1H, dt, J=1 Hz and 8 Hz, 4CH); 8.54 (1H, dd, J=1 Hz and 5 Hz, 6CH); 8.93 (1H, dd, J=1 Hz, 2CH).

b) 1-Methyl-3-[4-(2-methyl-1,3-oxazol)-yl]pyridinium iodide

A solution of the foregoing pyridine (3.16 g, 19.8 mmol) and methyl iodide (1.5 ml, 23.7 mmol) in acetone (20 ml) was stirred at 20° for 3 days. The precipitate was collected, washed with cold acetone and dried to yield the title compound as pale orange crystals, (5.12 g, 86%), m.p. 180°–182° (dec). (Found: C, 39.71; H, 3.68; N, 9.21; $C_{10}H_{11}IN_2O$ requires: C, 39.76; H, 3.67; N, 9.27%); δ (360 MHz, D$_2$O) 2.58 (3H, s, oxazole CH$_3$); 4.49 (3H, s, NCH$_3$); 8.10 (1H, dd, J=6 Hz and 8 Hz, 5CH; 8.43 (1H, s, oxazole CH); 8.72–8.78 (2H, m, 4CH and 6CH); 9.11 (1H, s, 2CH).

c)

1-Methyl-3-[4-(2-methyl-1,3-oxazol)-yl]-1,2,5,6-tetrahydropyridine hydrogen fumarate A solution of the foregoing pyridinium salt (5.54 g, 18.3 mmol) in water (50 ml) and ethanol (50 ml) was treated with sodium borohydride (0.70 g, 18.4 mmol) exactly as described in Example 17, to yield the title compound free base after chromatography as an oil (2.25 g, 69%). A portion of this material (0883 g, 4.96 mmol) was treated with fumaric acid (0.546 g, 4.71 mmol) in methanol, concentrated and cooled to yield the title compound as colourless needles (833 mg), m.p. 144°–146° (Found: C, 56.92; H, 6.23; N, 9.36; $C_{10}H_{14}N_2O \cdot C_4H_4O_4$ requires: C, 57.14; H, 6.17; N, 9.52%); m/e 178 (M+); δ (360 MHz, D$_2$O) 2.44 (3H, s, oxazole CH$_3$); 2.62–2.72 (2H, m, 5CH$_2$); 3.02 (3H, s, NCH$_3$); 3.24–3.32 (1H, m, 6CH); 3.58–3.65 (1H, m, 6CH); 3.89 (1H, dq, J=1 Hz and 16 Hz, 2CH); 4.10 (1H, d, J=16 Hz, 2CH); 6.45–6.49 (1H, m, 4CH); 6.65 (2H, s, HO$_2$CC$\underline{H}$=C$\underline{H}$CO$_2$H); 7.73 (1H, s, oxazole CH).

EXAMPLE 20

3-[4-(2-Methyl-1,3-oxazol)-yl]-1,2,5,6-tetrahydropyridine hydrogen oxalate a)

1-Ethenyloxycarbonyl-3-[4-(2-methyl-1,3-oxazol-yl]-1,2,5,6-tetrahydropyridine

A solution of 1-methyl-3-[4-(2-methyl-1,3-oxazol)-yl]-1,2,5,6-tetrahydropyridine (1.19 g, 10.7 mmol), from Example 19 in 1,2-dichloroethane (15 ml) was treated with vinyl chloroformate (1.3 ml, 13.9 mmol) exactly as described in Example 16 to yield the title compound as an oil (1.54 g, 61%). (Found: M+, 234.1010; $C_{12}H_{14}N_2O_3$ requires 234.1004); δ (360 MHz, CDCl$_3$) 2.33–2.38 (2H, m, 5CH$_2$); 2.46 (3H, s, CH$_3$); 3.62–3.68 (2H, m, 6CH$_2$); 4.18–4.23 (2H, m, 2CH$_2$); 4.48 (1H, dd, J=2 Hz and 6 Hz, CO$_2$CH=CH, trans to O); 4.82 (1H, d, J=14 Hz CO$_2$CH=CH, cis to O); 6.53-6.57 (1H, m, 4CH); 7.25 (1H, dd, J 6 Hz and 14 Hz, CO$_2$CH=CH$_2$); 7.44 (1H, s, oxazole CH).

b) 3-[4-(2-Methyl-1,3,-oxazol)-yl]-1,2,5,6-tetrahydropyridine hydrogen oxalate

A solution of the foregoing carbamate (1.42 g, 6.07 mol) in methanolic hydrogen chloride (50 ml) was stirred at 20° for 6 h and evaporated to dryness. The residue was partitioned between aqueous potassium carbonate and dichloromethane, the organic layer dried over magnesium sulphate and evaporated. Column chromatography of the residue on grade III alumina in dichloromethane/methanol (99:1) yielded the title compound free base (755 mg, 76%), which was converted to the hydrogen oxalate salt and recrystallised from methanol (972 mg, 63% yield). m.p. 204°-206° (Found: C, 49.80; H, 5.65; N, 10.52; C$_9$H$_{12}$N$_2$O. C$_2$H$_2$O$_4$.0.6H$_2$O requires: C, 49.85; H, 5.78; N, 10.57%); m/e 164 (M+); δ (360 MHz, D$_2$O) 2.45 (3H, s, CH$_3$); 2.54-2.60 (2H, m, 5CH$_2$); 3.39 (2H, t, J=6Hz, 6CH$_2$); 3.93 (2H, d, J=2 Hz, 2CH$_2$); 6.46-6.49 (1H, m, 4CH); 7.72 (1H, s, oxazole CH).

EXAMPLE 21

1-Methyl-3-[2-(4-methyl-1,3-oxazol)-yl]-1,2,5,6-tetrahydropyridine sesquifumarate a) 3-[2-(4-Methyl-1,3-oxazol)-yl]pyridine A mixture of 3-cyanopyridine (31.2 g, 0.30 mol) and =freshly distilled propargyl alcohol (84 g, 1.50 mol) was added dropwise with stirring to concentrated sulphuric acid (70 ml), cooled in ice/salt, over 2.5 h, keeping the temperature below 5°. When the addition was complete the mixture was allowed to warm to 20° over several hours, and stirred for 8 days. The dark mixture was poured into ice/water (1000 ml), filtered through Hyflo and washed with ethyl acetate (500 ml). The aqueous layer was basified by cautious addition of a solution of sodium hydroxide (105 g, 2.63 mol) in water (250 ml), extracted with dichloromethane (4×500 ml), the combined extracts dried over magnesium sulphate and evaporated. Column chromatography of the residue on silica in dichloromethane/methanol (98:2) gave unreacted cyanopyridine as the first component; increasing to 95:5 yielded the desired oxazole (1.76 g, 3.7%) as a crystalline solid. An analytical sample was recrystallised from hexane, m.p. 39°-42° (Found: C, 66.69; H, 5 18; N, 17.14; C$_9$H$_8$N$_2$O.0.1H$_2$O requires: C, 66.74; H, 5.10; N, 17.30%); m/e 160 (M+); δ (360 MHz, CDCl$_3$) 2.26 (3H, d, J=1 Hz, CH$_3$); 7.38 , (1H, ddd, J=1 Hz, 5 Hz and 8 Hz, 5CH); 7.48 (1H, q, J=1 Hz, oxazole CH); 8.28 (1H, dt, J=1 Hz and 8 Hz, 8.67 (1H, dd, J=1 Hz and 5 Hz, 6CH); 9.25 (1H, t, J 1 Hz, 2CH).

b) 1-Methyl-3-[2-(4-methyl-1,3-oxazol)-yl pyridinium iodide

Methyl iodide ( 1.2 ml, 18.9 mmol ) was added to a stirred solution of the foregoing pyridine (2.52 g, 15.8 mmol ) in acetone ( 16 ml ) . After 4 days at 20° the precipitate was collected, washed with acetone and dried to yield the title compound as a pale yellow powder (3.71 g, 78%) m.p 207°-209° (dec) (Found: C, 39.94; H, 3.72; N, 9.05; C$_{10}$H$_{11}$IN$_2$O requires: C, 39.76; H, 3.67; N, 9.27%); δ (360 MHz, D$_2$O) 2.28 ( 3H, d, J=1 Hz, oxazole CH$_3$ ); 4.52 ( 3H, s, NCH$_3$); 7.87 (1H, q, J=1 Hz, oxazole CH); 8.21 (1H, dd, J=6 Hz and 8 Hz, 5CH); 8.90 (1H, d, J=6 Hz, 4CH); 8.98 (1H, d, J=8 Hz, 6CH); 9.39 (1H, s, 2CH).

c) 1-Methyl-3-[2-(4-methyl-1,3-oxazol)-yl]-1,2,5,6-tetrahydropyridine sesquifumarate A solution of the foregoing pyridinium salt (4.21 g, 13.9 mmol) in water (40 ml) and ethanol (40 ml) was treated with sodium borohydride (0.53 g, 13.9 mmol) exactly as described in Example 17 to yield the title compound free base after chromatography (1.48 g., 8.31 mmol, 60%), which was treated with fumaric acid (0.940 g, 8.10 mmol) in methanol and concentrated to yield the sesquifumarate salt (940 mg), m.p. 145°-146° (Found: C, 54.36; H, 5.74; N, 7.89; C$_{10}$H$_{14}$N$_2$O. 1.5 C$_4$H$_4$O$_4$ requires: C, 54.54; H, 5.72; N, 7.95%); m/e 178 (M+); δ (360 MHz, D$_2$O) 2.13 (3H, d, J=1 Hz, oxazole CH$_3$); 2.71-2.77 (2H, m, 5CH$_2$); 3.06 (3H, s, NCH$_3$); 3.26-3.44 (1H, m, 6CH); 3.61-3.69 (1H, m, 6CH); 3.93-4.00 (1H, m, 2CH); 4.32 (1H, d, J=16 Hz, 2CH); 6.71 (3H, s, HO$_2$CCH=CHCO$_2$H); 6.90-6.96 (1H, m, 4CH); 7.56 (1H, q, J=1 Hz, oxazole CH).

EXAMPLE 22

1-Methyl-3-[5-(2-methyl-1,3-oxazole)-yl]-1,2,5,6-tetrahydropyridine sesquifumarate a) 3-[5-(2-Methyl-1,3-oxazol)-yl]pyridine Crude 3-(aminoacetyl)pyridine dihydrochloride (10.0 g, 47.8 mmol), prepared by the method of G. R. Clemo et al., J. Chem. Soc., 1938, 753, was suspended in triethyl orthoacetate (120 ml) and heated under reflux in an oil bath at 140° for 4 h. The cooled solution was decanted from some undissolved tar and evaporated. The residue was dissolved in water (100 ml), stirred for 10 min then basified with solid sodium carbonate and extracted with dichloromethane (4×100 ml). The combined extracts were dried over magnesium sulphate, evaporated and purified by column chromatography on silica in dichloromethane/methanol (98:2) to yield the title oxazole which crystallised on standing (5.33 g 69%) m.p. 29°-33° (Found: C, 66.7; H, 5.3; N, 16.9; C$_9$H$_8$N$_2$O.0.15H$_2$O requires: C, 66.4; H, 5.1; N, 17.2%); m/e 160 (M+); δ (250 MHz, CDCl$_3$) 2.56 (3H, s, CH$_3$); 7.30 (1H, s, oxazole CH); 7.34 (1H, ddd, J=1 Hz, 5 Hz and 8 Hz, 5CH); 7.88 (1H, dt, J=1 Hz and 8 Hz, 4CH); 8.54 (1H, dd, J=2 Hz and 5 Hz, 6CH); 8.88 (1H, dd, J=2 Hz and 1 Hz, 2CH).

b) 1-Methyl-3-[5-(2-methyl-1,3-oxazol)-yl]pyridinium iodide

Methyl iodide (2.2 1, 35.6 mmol) was added to a stirred solution of the foregoing pyridine (4.75 g, 29.7 mmol) in acetone (30 ml). After 4 days at 20° the precipitate was collected, washed with acetone and dried to give the title compound as off-white plates (7.06 g, 79%), m.p. 189°-191° (Found: C, 39.67; H, 3.69; N, 9.22; C$_{10}$H$_{11}$IN$_2$O requires: C, 39.76; H, 3.67; N, 9.27%); δ (360 MHz, D$_2$O) 2.60 (3H, s, oxazole CH$_3$); 4.45 (3H, s, NCH$_3$); 7.73 (1H, s, oxazole CH); 8.10 (1H, dd, J=6 Hz and 7 Hz, 5CH); 8.78-8.86 (2H, m, 4CH and 6CH); 9.16 (1H, s, 2CH).

c)

1-Methyl-3-[5-(2-methyl-1,3-oxazol)-yl]-1,2,5,6-tetrahydropyridine sesquifumarate A solution of the foregoing pyridinium salt (6.96 g, 23.0 mmol) in water (65 ml) and ethanol (65 ml) was treated with sodium borohydride (0.88 g, 23 mmol), exactly as described in Example 17 to yield the title compound free base after chromatography (2.90 g, 16.3 mmol, 71%). To this was added fumaric acid (1.85 g, 15.9 mmol) in methanol (40 ml), the solvent evaporated, the residue triturated with ether and recrystallised from propan-2-ol to give the sesquifumarate (1.74 g), m.p. 140°–142° (Found: C, 54.37; H, 5.79; N, 7.90; $C_{10}H_{14}N_2O.1.5\ C_4H_4O_4$ requires: C, 54.54; H, 5.72; N, 7.95%); m/e 178 (M+); δ (360 MHz $D_2$)) 2.45 (3H, s, oxazole $CH_3$); 2.62–2.74 (2H, m, 5$CH_2$); 3.03 (3H, s, N$CH_3$); 3.24–3.33 (1H, m, 6CH); 3.60–3.68 (1H, m, 6CH); 3.90 (1H, dq, J=1 Hz and 16 Hz, 2CH); 4.16 (1H, d, J=16 Hz, 2CH); 6.44–6.49 (1H, m, 4CH); 6.71 (3H, s, $HO_2CC\underline{H}=C\underline{H}CO_2H$); 6.94 (1H, x, oxazole CH).

EXAMPLE 23

3-[2-(4-Methyl-1,3-oxazol)-yl]-1,2,5,6-tetrahydropyridine hydrogen oxalate a)

1-Ethenyloxycarbonyl-3-[2-(4-methyl-1,3-oxazol)-yl]-1,2,5,6-tetrahydropyridine A solution of 1-methyl-3-[2-(4-methyl-1,3-oxazol)-yl]-1,2,5,6-tetrahydropyridine (1.20 g, 6.74 mmol), from Example 21, in 1,2-dichloroethane (10 ml) was treated with vinyl chloroformate (0.80 ml, 8.8 mmol) exactly as described in Example 16 to yield the title compound as a waxy solid (1.11 g, 70%) δ (360 MHz, CDCl$_3$) 2.19 (3H, s, $CH_3$); 2.34–2.41 (2H, m, 5$CH_2$); 3.60–3.69 (2H, m, 6$CH_2$); 4.43–4.51 (3H, m, 2$CH_2$ and $CO_2CH=C\underline{H}$, trans to O); 4.86 (1H d J=14 Hz, $CO_2CH=C\underline{H}$, cis to O); 6.80–6.85 (1H, m, 4CH); 7.23 (1H, dd, J=6 Hz and 14 Hz, $CO_2C\underline{H}=CH_2$); 7.31 (1H, s, oxazole CH).

b)

3-[2-(4-Methyl-1,3-oxazol)-yl]-1,2,5,6-tetrahydropyridine hydrogen oxalate

A solution of the foregoing carbamate (1.03 g, 4.40 mmol) in methanolic hydrogen chloride (30 ml) was stirred at 20° for 15 h, and evaporated to dryness. The residue was partitioned between aqueous potassium carbonate and dichloromethane, the organic layer dried over magnesium sulphate and evaporated to yield the title compound free base (683 mg, 95%). This material was treated with oxalic acid (360 mg, 4.0 mmol) and recrystallised from methanol to give the hydrogen oxalate salt (725 mg, 65% yield). m.p. 176°–178°. (Found: C, 57.89; H, 5.54; N, 10.95; $C_9H_{12}N_2O.\ C_2H_2O_4$ requires: C, 51.97; H, 5.55; N, 11.02%). m/e 164 (M+); δ (250 MHz, $D_2O$) 2.14 (3H, s, $CH_3$); 2.61–2.72 (2H, m, 5$CH_2$); 3.43 (2H, t, J=6 Hz, 6$CH_2$); 4.08 (2H, d, J=2 Hz, 2$CH_2$); 6.92–6.98 (1H, m, 4CH); 7.56 (1H, s, oxazole CH).

EXAMPLE 24

3-[5-(2-Methyl-1,3-oxazol)-yl]-1,2,5,6-tetrahydropyridine hydrogen oxalate a)

1-Ethenyloxycarbonyl-3-[5-(2-methyl-1,3-oxazol)-yl]-1,2,5,6-tetrahydropyridine A stirred solution of 1-methyl-3-[5-(2-methyl-1,3-oxazol)-yl]-1,2,5,6-tetrahydropyridine (2.30 g, 12.9 mmol), from Example 22, in 1,2-dichloroethane (18 ml) at −5° was treated with vinyl chloroformate (1.55 ml, 16.8 mmol). causing a precipitate to form. After 15 min the mixture was heated to reflux for 4 h, cooled, diluted with dichloromethane (50 ml) and washed in turn with 0.5M hydrochloric acid and saturated sodium hydrogen carbonate. The organic layer was dried over magnesium sulphate and evaporated to give the crude product (570 mg) which was purified by column chromatography on silica in dichloromethane/ethyl acetate (95:5). The third-eluted component was the desired product (22 mg), as a gum. δ (250 MHz, CDCl$_3$) 2.32–2.41 (2H, m, 5$CH_2$); 2.47 (3H, s, $CH_3$); 3.60–3.71 (2H, m, 6$CH_2$); 4.19–4.26 (2H, m, 2$CH_2$); 4.50 (1H, dd, J=6 Hz, $CO_2CH=C\underline{H}$, trans to O); 4.84 (1H, d, J=14 Hz, $CO_2CH=C\underline{H}$, cis to O): 6.29–6.38 (1H, m, 4CH); 6.83 (1H, s, oxazole CH); 7.25 (1H, dd, J=6 Hz and 14 Hz, $CO_2C\underline{H}=CH_2$).

b)

3-[5-(2-Methyl-1,3-oxazol)-yl-1,2,5,6-tetrahydropyridine hydrogen oxalate

A solution of the foregoing carbamate (20 mg, 0.086 mmol) in methanolic hydrogen chloride was stirred at 20° for 3 h, then partitioned between aqueous potassium carbonate and dichloromethane. The organic layer was dried over potassium carbonate and evaporated to yield the title compound (12 mg, 85%), which was converted to the hydrogen oxalate and crystallised from ethanol/ether, m.p. 110°–122°. m/e 164 (M+); δ (250 MHz, $D_2O$) 2.54 (3H, s, $CH_3$); 2.54–2.67 (2H, m, 5$CH_2$); 3.41 (2H, t, J=6 Hz, 6$CH_2$); 3.95–4.02 (2H, m, 2$CH_2$); 6.52–6.60 (1H, m, 4CH); 7.11 (1H, s, oxazole CH).

EXAMPLE 25

Tablet Preparation

Tablets containing 1.0, 2.0, 25.0, 26.0, 50.0 and 100.0 mg, respectively, of the following compounds are prepared as illustrated below:

3-[4-(1,3-Thiazol)-yl]quinuclidine hydrogen oxalate
3-[2-(4-Methyl-1,3-oxazol)-yl]quinuclidine hydrochloride
3-[2-(5-methyl-1,3-oxazol)yl]-1,2,5,6-tetrahydropyridine hydrochloride
3-[4-(2-Methyl-1,3-thiazol)-yl]-1,2,5,6-tetrahydropyridine dihydrochloride

| TABLE FOR DOSES CONTAINING FROM | Amount-mg | | |
| --- | --- | --- | --- |
| 1–25 MG OF THE ACTIVE COMPOUND | | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |
| 26–100 MG OF THE ACTIVE COMPOUND | | | |
| Active Compound | 26.0 | 50.0 | 100.0 |

| TABLE FOR DOSES CONTAINING FROM | Amount-mg | | |
|---|---|---|---|
| Microcrystalline Cellulose | 52.0 | 100.0 | 200.0 |
| Modified food corn starch | 2.21 | 4.25 | 8.5 |
| Magnesium stearate | 0.39 | 0.75 | 1.5 |

All of the active compound, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.00 mg, 50.0 mg and 100.0 mg of active ingredient per tablet.

What is claimed is:

1. A method for the treatment of neurological and mental illnesses whose clinical manifestations are due to involvement of cholinergic neurones, which comprises administering to a patient in need of such treatment an effective muscarinic agonist amount of a 1,3-oxazole or 1,3-thiazole of structural formula I or a pharmaceutically acceptable salt or prodrug thereof:

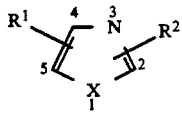

wherein
X represents oxygen or sulphur;
$R^1$ represents a non-aromatic azacyclic or azabicyclic ring system in the 2, 4 or 5 position; and
$R^2$ is in the 2, 4 or 5 position and is selected from the group consisting of halogen, —$CF_3$, —$OR^7$, —$NR^7R^8$, —$NHOR^7$, —$NHNH_2$, —CN, —$CO_2R^7$, —$CONR^7R^8$, and an unsaturated hydrocarbon selected from the group consisting of $C_{2-15}$ alkenyl, $C_{2-15}$ alkynyl, phenyl and phenyl-$C_{1-3}$ alkyl; wherein $R^7$ and $R^8$ independently represent hydrogen or $C_{1-2}$ alkyl provided that, when $R^2$ is methyl and $R^1$ is in the 2-position, then $R^1$ does not represent an unsubstituted exo-1-azabicyclo[2.2.1]hept-3-yl, or exo-1-azabicyclo[3.2.1]-oct-6-yl group.

2. A method for the treatment of severe painful conditions, which comprises administering to a patient in need of such treatment an effective analgesic amount of a compound of formula I as defined in claim 1, or a pharmaceutically acceptable salt or prodrug thereof.

3. A compound of formula II

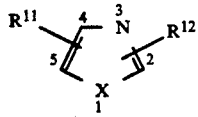

wherein
X is oxygen or sulphur,
$R^{11}$ represents a non-aromatic azacyclic or azabicyclic ring system containing 4–10 ring atoms attached to the 2,4,5 position of the thiazole ring, wherein the ring nitrogen can be alkylated by $C_{1-4}$ alkyl and said aza ring can be substituted by $C_{1-4}$ alkyl, halo, $C_{1-4}$ alkoxy, hydroxy, carboxy or carbonyl; and
$R^{12}$ is attached to the 2,4, or 5 position of the thiazole ring and is selected from the group consisting of halogen, —$CF_3$, —$OR^7$, —$NR^7R^8$, —$NHOR^7$, —$NHNH_2$, —CN, —$CO_2R^7$ and —$CONR^7R^8$ and a saturated or unsaturated hydrocarbon selected from the group consisting of $C_{1-15}$ alkyl, $C_{2-15}$ alkenyl, $C_{2-15}$ alkynyl, phenyl and phenyl-$C_{1-3}$ alkyl, wherein the hydrocarbon can be substituted by a substituent selected from halo, —$OR^6$, —$CF_3$, —$NR^6R^9$, $NO_2$, phenyl, wherein the phenyl can be substituted by a substituent selected from chloro, bromo, methoxy, $C_{1-6}$ alkyl, methoxycarbonyl, trifluoromethyl, nitro and —$NR^6R^7$, keto, —$SR^6$, $CO_2R^6$, and —$CONR^6R^9$; wherein $R^6$ is H or $C_{1-6}$ alkyl and $R^9$ is H, $C_{1-6}$ alkyl or —$COCH_3$; wherein $R^7$ and $R^8$ are independently hydrogen or $C_{1-2}$ alkyl;
provided that when $R^{12}$ is present in the 2-position and represents amino, alkylamino, dialkylamino or alkylcarbonylamino, then $R^{11}$ present in the 4-position, does not represent optionally N-substituted piperidin-3-yl or 1,2,5,6-tetrahydropyridin-3-yl;
provided also that when $R^{12}$ is methyl and $R^{11}$ is in the 2-position, then $R^{11}$ does not represent an unsubstituted exo-1-azabicyclo[2.2.1]hept-3-yl or exo-1-azabicyclo[3.2.1]-oct-6-yl group.

4. A compound according to claim 3 represented by formula (III):

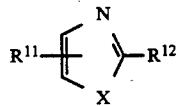

wherein X, $R^{11}$ and $R^{12}$ are as defined in claim 3.

5. A compound according to claim 3 represented by the formula (IV):

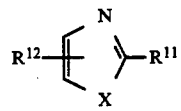

wherein X, $R^{11}$ and $R^{12}$ are as defined in claim 3.

6. A compound according to claim 3 wherein $R^{11}$ is selected from the group consisting of tetrahydropyridine, 1-azanorbornane, quinuclidine and 1-azabicyclo[3.2.1]octane, any of which groups $R^{11}$ may be substituted with $C_{1-3}$ alkyl or hydroxy.

7. A compound according to claim 3, wherein $R^{12}$ is selected from the group consisting of hydrogen, methyl, ethyl, amino and hydroxy.

8. A pharmaceutical composition comprising an effective muscarinic agonist amount of a compound according to claim 3 in association with a pharmaceutically acceptable carrier.

9. A pharmaceutical composition according to claim 8 further comprising a peripheral cholinergic antagonist.

10. A compound selected from the following:
3-[4-(2-amino-1,3-thiazol)-yl]quinuclidine;
3-[4-(1,3-thiazol)-yl]quinuclidine;
3-[4-(2-amino-1,3-thiazol)-yl]pyrrolidine;
3-[4-(2-amino-1,3-thiazol)-yl]-1-methylpyrrolidine;

3-[4-(2-methyl-1,3-thiazol)-yl]-quinuclidine; 3-[4-(2-hydroxy-1,3-thiazol)-yl]quinuclidine;
3-[5-(2-methyl-1,3-thiazol)-yl]quinuclidine;
3-[4-(2-amino-1,3-thiazol)-yl]-1-azabicyclo[2.2.1]-heptane;
3-[5-(2-methyl-1,3-oxazol)-yl]quinuclidine;
3-[5-(2-methyl-1,3-oxazol)-yl]-1-azabicyclo[2.2.1]-heptane;
3-[4-(2-methyl-1,3-oxazol)-yl]quinuclidine;
3-[4-(2-amino-1,3-oxazol)-yl]quinuclidine;
3-[2-(4-methyl-1,3-thiazol)-yl]-1-azabicyclo[2.2.2]oct-2ene;
3-hydroxy-3-[2-(4-methyl-1,3-oxazol)-yl]quinuclidine;
3-hydroxy-3-(2-(1,3-oxazol)-yl]quinuclidine;
3-hydroxy-3-[2-(4-ethyl-1,3-oxazol)-yl]quinuclidine;
3-[2-(4-ethyl-1,3-oxazol)-yl]quinuclidine;
3-hydroxy-3-[2-(4-methyl-1,3-thiazol)-yl]quinuclidine;
1-methyl-3-[2-(5-methyl-1,3-oxazol)-yl]piperidine;
1-methyl-3-[2-(5-methyl-1,3-oxazol)-yl]-1,2,5,6-tetrahydropyridine;
3-[2-(5-methyl-1,3-oxazol)-yl]-1,2,5,6-tetrahydropyridine;
1-methyl-3-[4-(2-methyl-1,3-thiazol)-yl]-1,2,5,6-tetrahydropyridine;
3-[4-(2-methyl-1,3-thiazol)-yl]-1,2,5,6-tetrahydropyridine;
1-methyl-3-[4-(2-methyl-1,3-oxazol)-yl]-1,2,5,6-tetrahydropyridine;
3-[4-(2-methyl-1,3-oxazol)-yl]-1,2,5,6-tetrahydropyridine;
1-methyl-3-[2-(4-methyl-1,3-oxazol)-yl]-1,2,5,6-tetrahydropyridine;
1-methyl-3-[5-(2-methyl-1,3-oxazol)-yl]-1,2,5,6-tetrahydropyridine;
3-[2-(4-methyl-1,3-oxazol)-yl]-1,2,5,6-tetrahydropyridine;
3-[5-(2-methyl-1,3-oxazol)-yl]-1,2,5,6-tetrahydropyridine; and salts and prodrugs thereof.

* * * * *